(12) United States Patent
Abel-Santos et al.

(10) Patent No.: US 9,079,935 B2
(45) Date of Patent: Jul. 14, 2015

(54) **REDUCING RISK OF CONTRACTING *CLOSTRIDIUM-DIFFICILE* ASSOCIATED DISEASE**

(71) Applicant: The Regents of the Nevada System of Higher Education on behalf of the University of Nevada, Las Vegas, Las Vegas, NV (US)

(72) Inventors: Ernesto Abel-Santos, Las Vegas, NV (US); Amber Howerton, Las Vegas, NV (US)

(73) Assignee: The Board of Regents of the Nevada System of Higher Education on Behalf of The University of Nevada, Las Vegas, Las Vegas, NV (US)

( * ) Notice: Subject to any disclaimer, the term of this patent is extended or adjusted under 35 U.S.C. 154(b) by 0 days.

(21) Appl. No.: 13/962,658

(22) Filed: Aug. 8, 2013

(65) Prior Publication Data

US 2014/0045808 A1     Feb. 13, 2014

Related U.S. Application Data

(60) Provisional application No. 61/682,505, filed on Aug. 13, 2012.

(51) Int. Cl.
*A61K 31/56* (2006.01)
*C07J 41/00* (2006.01)
*C07J 31/00* (2006.01)

(52) U.S. Cl.
CPC .............. *C07J 41/0061* (2013.01); *C07J 31/00* (2013.01); *C07J 31/006* (2013.01); *C07J 41/00* (2013.01)

(58) Field of Classification Search
None
See application file for complete search history.

(56) References Cited

U.S. PATENT DOCUMENTS

| 5,824,698 | A | 10/1998 | Hasler et al. |
| 2007/0112048 | A1 | 5/2007 | Bavari et al. |
| 2008/0254010 | A1* | 10/2008 | Sasser et al. ............... 424/93.44 |
| 2011/0086797 | A1 | 4/2011 | Dworkin |
| 2011/0183360 | A1 | 7/2011 | Rajagopal et al. |
| 2011/0229583 | A1 | 9/2011 | Tran et al. |
| 2011/0280847 | A1 | 11/2011 | Sorg et al. |
| 2012/0020950 | A1 | 1/2012 | Davis et al. |

FOREIGN PATENT DOCUMENTS

| WO | WO02060879 A1 | 8/2002 |
| WO | WO03105846 A1 | 12/2003 |
| WO | WO2004041209 A1 | 5/2004 |
| WO | WO2006076009 A1 | 7/2006 |
| WO | WO2007056330 A1 | 5/2007 |
| WO | WO2007148093 A1 | 12/2007 |

OTHER PUBLICATIONS

STN CAS RN 145-42-6 (entered STN Nov. 16, 1984).*

* cited by examiner

*Primary Examiner* — Craig Ricci
*Assistant Examiner* — Jared D Barsky
(74) *Attorney, Agent, or Firm* — Ballard Spahr LLP

(57) ABSTRACT

A method of treating a patient to reduce risk of developing *Clostridium difficile*-associated disease or reducing existing *Clostridium difficile*-associated disease in a mammalian subject involves administering to a mammalian subject an effective amount of a germination-inhibiting compound derived from taurocholate. Novel compounds of this class are also provided.

3 Claims, 15 Drawing Sheets

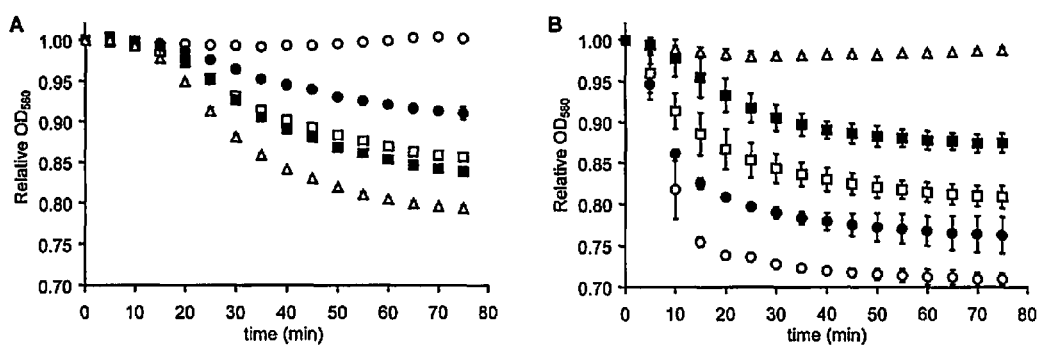
Figure 1. Germination kinetic graphs showing agonistic and antagonistic behavior of molecules with *C. difficile* spores.

Figure 2. Amino acids assessed for activation or inhibition of glycine-mediated germination in *C. difficile* spores.

Figure 3. Comparison of amino acids as agonists of *C. difficile* spore germination.

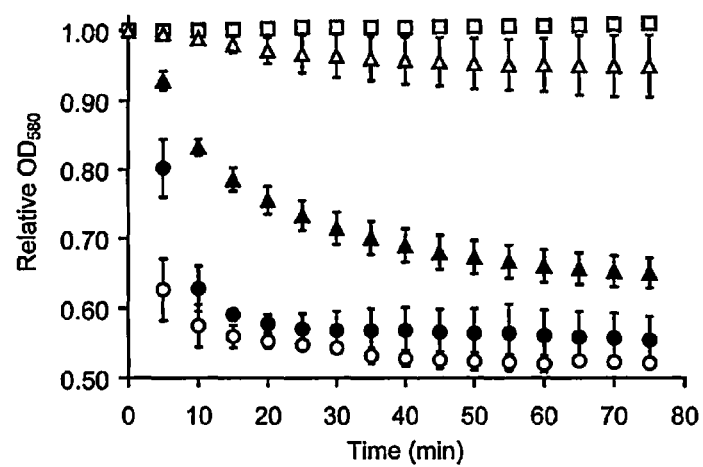
Figure 4. Germination kinetic graph showing behavior of *C. difficile* spores and germinants in buffer and complex media.

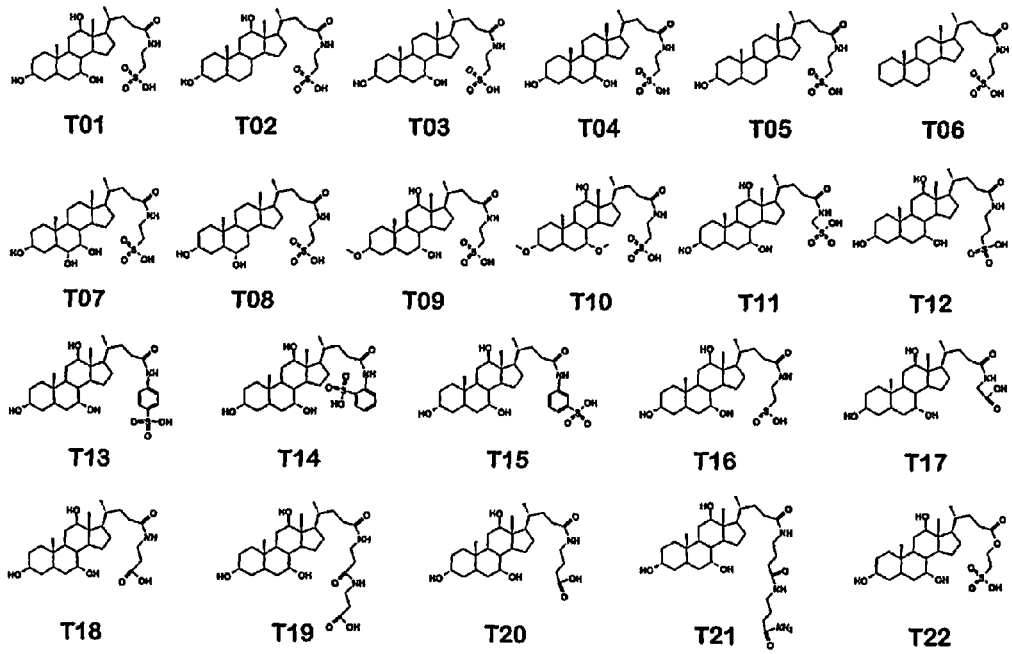
Figure 5. A chart of taurocholate analogs assessed for activation or inhibition of taurocholate-mediated germination in *C. difficile* spores.
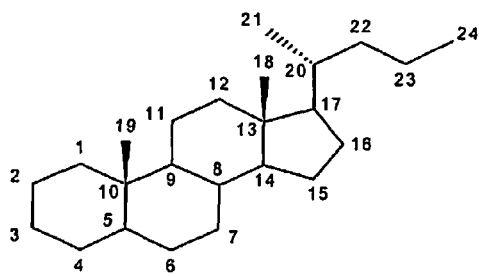
Figure 6. A generic structural formula showing the central core and ring positions on a taurocholate molecule.

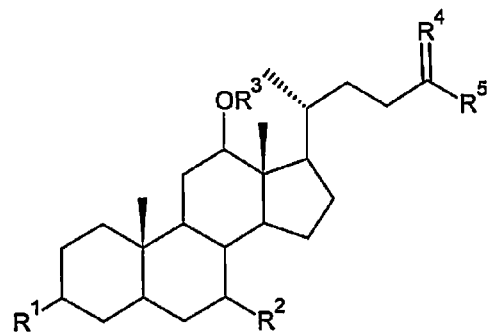
Figure 7. A more specific central core nucleus showing at least the major positions on the taurocholate central core on which substituents are placed within the scope of the present technology.

Table 3. Effect of taurocholate hydroxyl groups on *C. difficile* spore germination

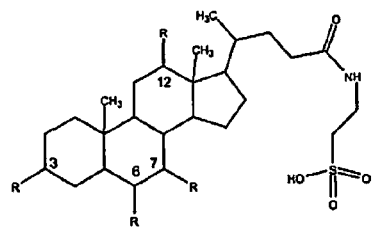

| Number | Position | | | | % Germination[a] | $IC_{50}$ (mM)[b] |
|---|---|---|---|---|---|---|
| | 3 | 6 | 7 | 12 | | |
| T01 | OH | H | OH | OH | 97.9 (1.9) | NA |
| T02 | OH | H | H | OH | 24.3 (1.8) | NA |
| T03 | OH | H | OH | H | 9.6 (0.4) | 0.51 (0.06) |
| T04 | OH | H | β-OH | H | 3.2 (1.7) | 0.32 (0.05) |
| T05 | OH | H | H | H | 2.3 (0.9) | NA |
| T06 | H | H | H | H | NA | NA |
| T07 | OH | OH | OH | H | 1.3 (0.5) | NA |
| T08 | OH | OH | H | H | 2.3 (2.4) | 0.41 (0.20) |
| T09 | OCH$_3$ | H | OH | OH | NA | NA |
| T10 | OCH$_3$ | H | OCH$_3$ | OH | NA | NA |

[a] *C. difficile* spores were individually treated with 6 mM glycine and 12 mM taurocholate analogs T01-T10. Percent germination was calculated based on taurocholate/glycine germination as 100%. Standard deviations are shown in parentheses.

[b] *C. difficile* spores were incubated with various concentrations of taurocholate analogs for 15 minutes prior to addition of 6 mM taurocholate and 12 mM glycine. $IC_{50}$ was calculated by plotting extent of germination vs. the logarithm of analog T02-T10 concentration. Standard deviations are shown in parentheses.

N/A, No activity under the conditions tested.

Figure 8 is Table 3. Effect of taurocholate hydroxyl groups on *C. difficile* spore germination.

Table 4. Effect of the taurocholate side chain on *C. difficile* spore germination

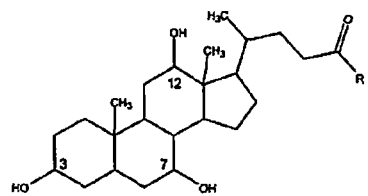

| Number | R | % Germination[a] | $IC_{50}$ (mM)[b] |
|---|---|---|---|
| T01 | $NH(CH_2)_2SO_3H$ | 97.9 (1.9) | NA |
| T11 | $NHCH_2SO_3H$ | 96.5 (2.1) | NA |
| T12 | $NH(CH_2)_3SO_3H$ | NA | NA |
| T13 | $NH(p\text{-}(C_6H_4))SO_3H$ | NA | NA |
| T14 | $NH(o\text{-}(C_6H_4))SO_3H$ | NA | NA |
| T15 | $NH(m\text{-}(C_6H_4))SO_3H$ | NA | 0.058 (0.035) |
| T16 | $NH(CH_2)_2SO_2H$ | NA | 0.64 (0.11) |
| T17 | $NHCH_2CO_2H$ | 59.5 (4.0) | NA |
| T18 | $NH(CH_2)_2CO_2H$ | NA | NA |
| T19 | $NH(CH_2)_2CONH(CH_2)_2CO_2H$ | NA | NA |
| T20 | $NH(CH_2)_3CO_2H$ | NA | 0.76 (0.11) |
| T21 | $NH(CH_2)_3CONH(CH_2)_3CO_2H$ | NA | 2.9 (0.41) |
| T22 | $O(CH_2)_2SO_3H$ | NA | 1.3 (0.05) |

Figure 9 is Table 4. Effect of the taurocholate side chain on *C. difficile* spore germination.

*Mice Treated with CamSA or chenodeoxycholate Show No Weight Changes.* Groups of five mice were treated with DMSO (□), 50 mg/kg chenodeoxycholate (◊), 50 mg/kg CamSA (Δ), or 300 mg/kg CamSA (o). Animal weight was obtained daily.

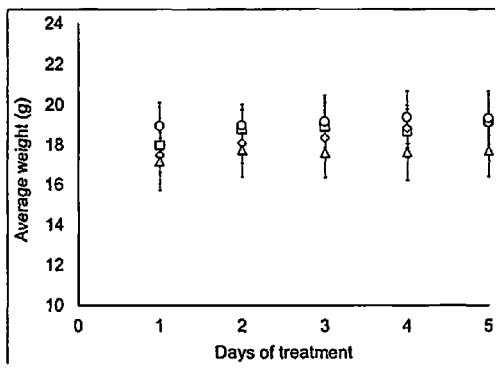

Figure 10. A graph evidencing that mice treated with CamSA or chenodeoxycholate show no weight changes with particular treatments.

*Graphic Results of Protection of Mice from CDI by Different Bile Salts.*

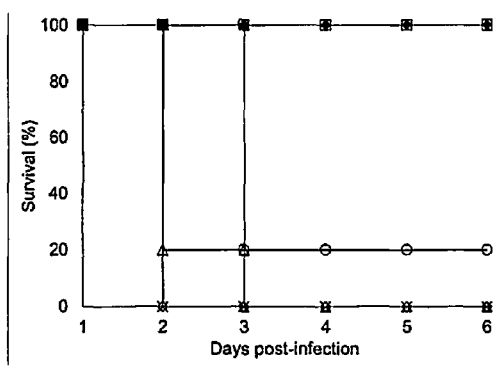

Figure 11. Graphic results of protection of mice from CDI by different bile salts. The data is shown in a Kaplan-Meier survival plot for treated *C. difficile* infected mice.

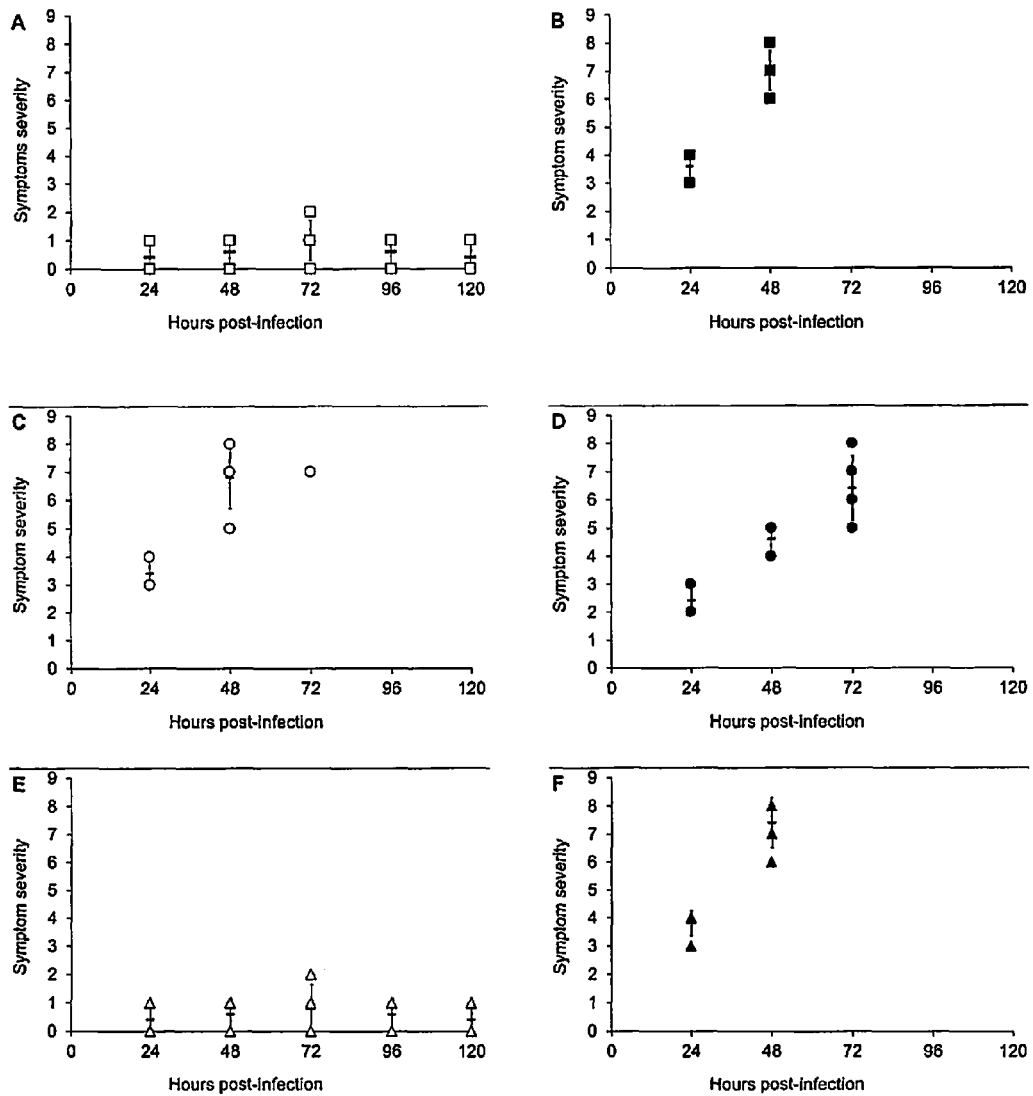
Figure 12. Graphic representations of signs of severity for *C. difficile* infected animals treated with different bile salts.

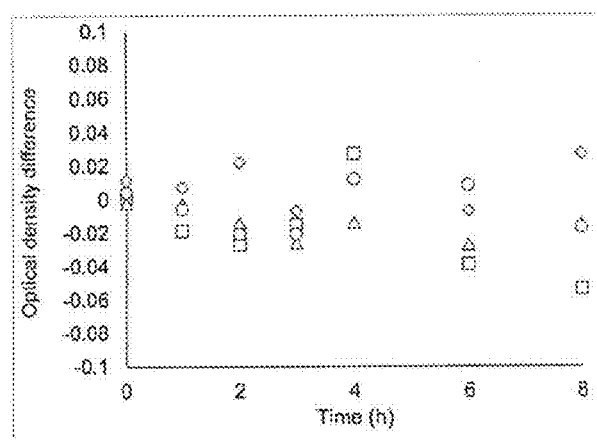
Figure 13. Graphically shows that CamSA does not affect vegetative bacterial growth.
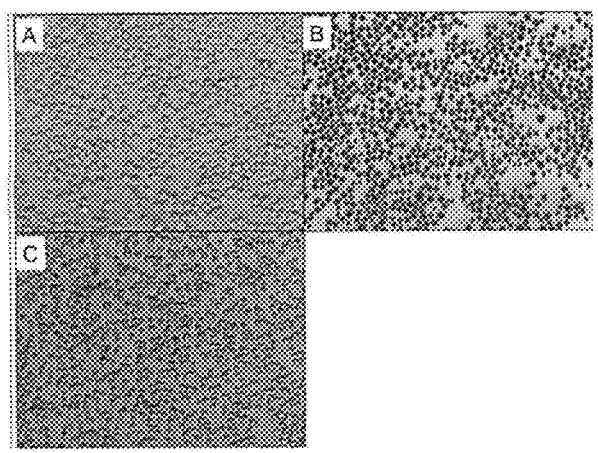
Figure 14. Graphically shows that CamSA is not toxic to mammalian cells.

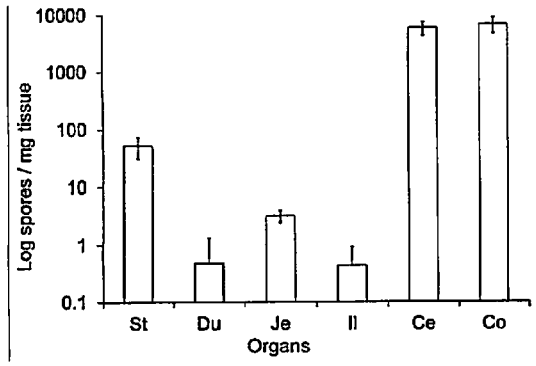
Figure 15. Graphically shows distribution of *C. difficile* spores in the GI tract of CamSA-treated animals. The stomach (St), duodenum (Du), jejunum (Je), and ileum (Il) showed negligible amounts of spores compared to the cecum (Ce) and colon (Co).
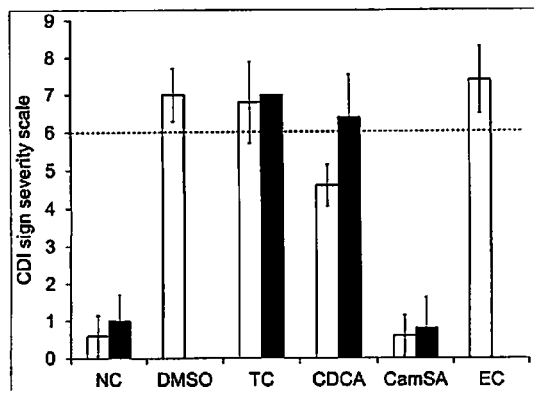
Figure 16. Graphic evidence that CamSA protects mice from CDI.

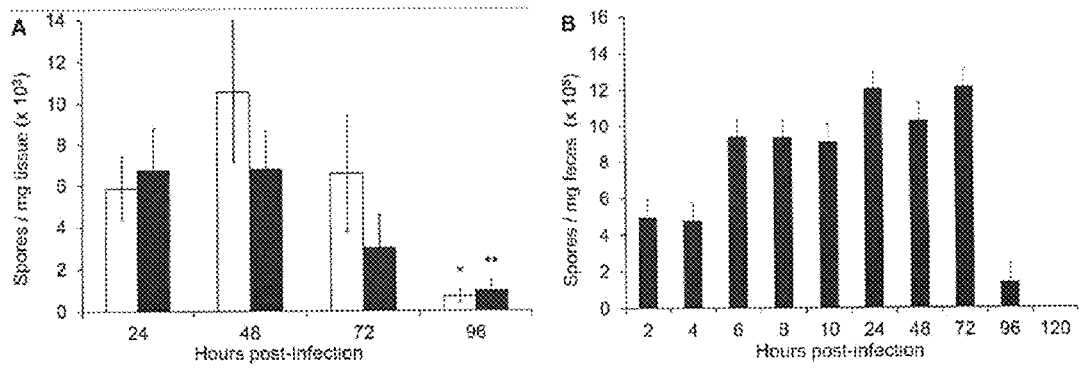
Figure 17. A graphic representation of data showing that *C. difficile* spores accumulate in the cecum, colon, and feces of CamSA-treated animals.
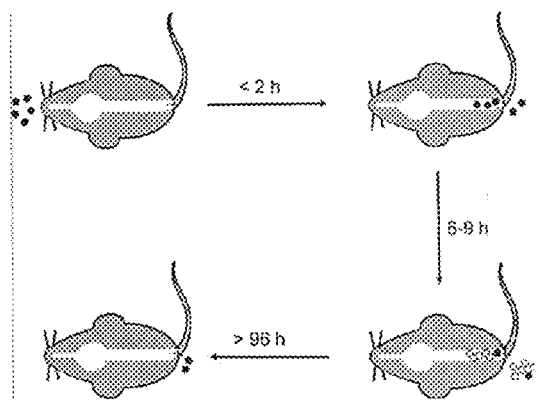
Figure 18. A time line model for CDI onset in mice. *C. difficile* spores (black circles) that are ingested by the host.

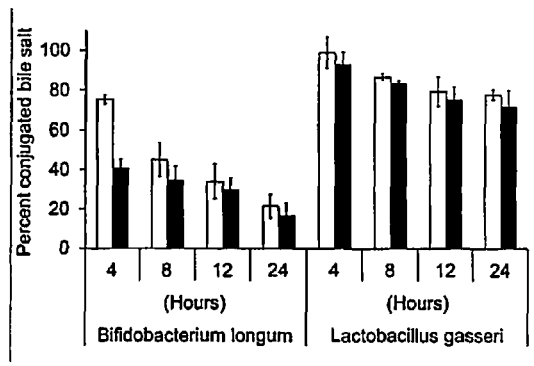
Figure 19. A graphic representation of the stability of CamSA and taurocholate towards bile salt hydrolases
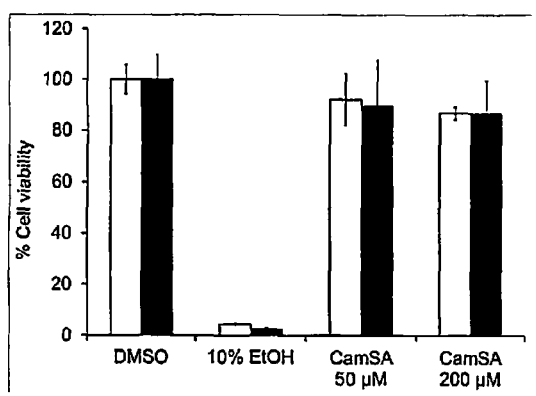
Figure 20. A graphic representation of the cytotoxicity of CamSA.

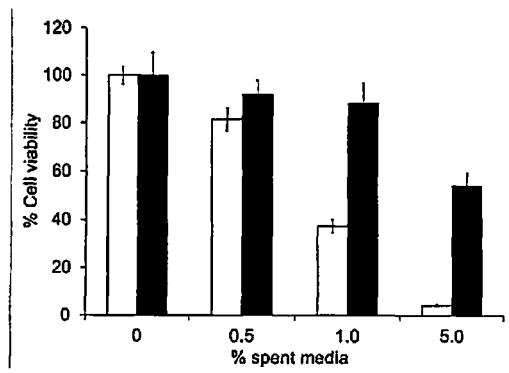
Figure 21. A graphic representation of inhibition of *C. difficile* toxin production by CamSA treatment.
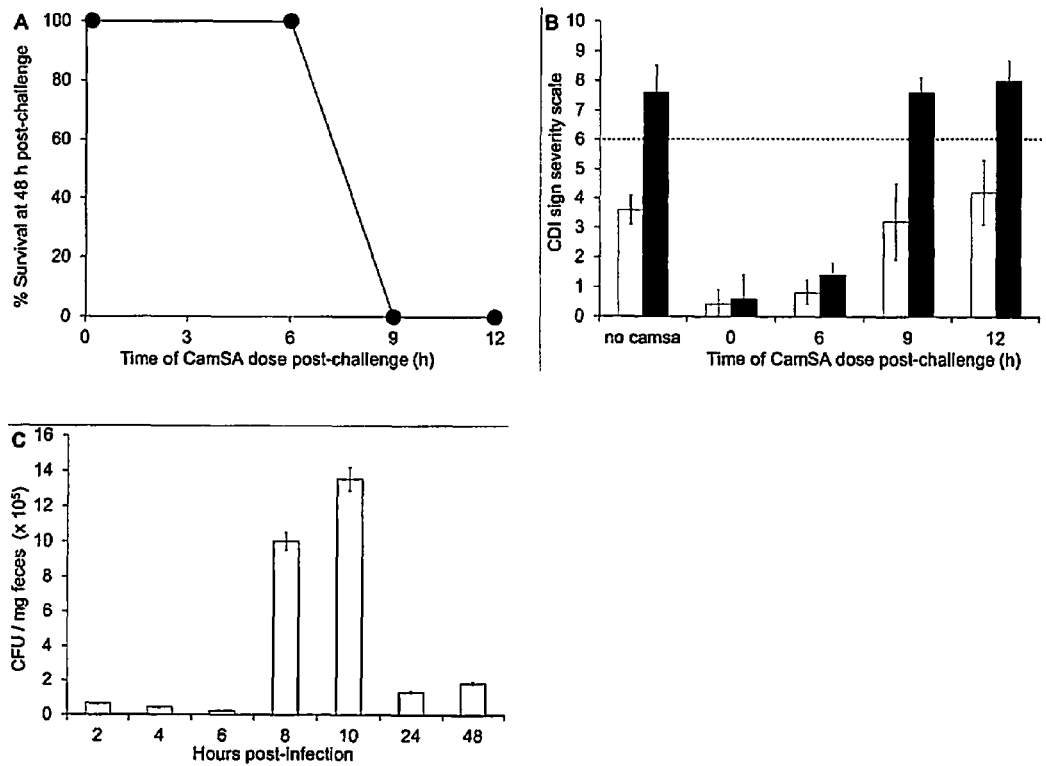
Figure 22. A graphic representation that CDI is established between 6 and 9 hours post-infection

REDUCING RISK OF CONTRACTING *CLOSTRIDIUM-DIFFICILE* ASSOCIATED DISEASE

RELATED APPLICATION DATA

This application claims priority from U.S. provisional Patent Application Ser. No. 61/682,505, filed 13 Aug. 2012, having the same title, inventors and assignee as the present application.

GOVERNMENT RIGHTS

This invention was made with government support under CHE0957400 awarded by the National Science Foundation. The government has certain rights in the invention.

BACKGROUND OF THE INVENTION

1. Field of the Invention

The present invention relates to compounds which are of use in the treatment of bacterial diseases and infections, to compositions containing those compounds and to methods of treating bacterial diseases and infections using the compounds. In particular, the compounds of the present invention are useful for the treatment of infection with, and diseases caused by, *Clostridium difficile*.

2. Background to the Invention

Spore Germination Inhibiting Drugs and *Clostridium difficile*

The development of antibacterial drugs represents one of the most important medical advances of the 20$^{th}$ Century. Previously untreatable diseases could now be readily controlled and it was felt that many diseases would be eradicated with these new wonder drugs. Despite these significant advances in treatment, infectious diseases are the third major cause of mortality in the USA (*Clin. Infect. Dis.*, 2004, 38, 1279-1286) and remain one of the most significant global healthcare problems. Rates of resistance in all of the major pathogenic bacteria are rising dramatically and of particular concern is the increasing number and severity of nosocomial infections (*Infectious Disease Society of America*, 2004, Bad Bugs, No Drugs). The emergence of multi-drug resistant pathogens has rendered many of the current frontline drugs completely ineffective in controlling many diseases.

A particular subset of bacterial pathogens of concern is those classified as spore-forming bacteria. Bacterial spores (endospores) are dormant, non-reproductive structures formed by bacteria in response to environmental stress. Once environmental conditions become favorable, the spores germinate and the bacteria proliferate. In the case of pathogenic bacteria, germination in a human host may result in disease. Germination of a spore, such as *Clostridium difficile* is the process in which a spore begins to grow into vegetative cells, and sporeling hyphae.

Bacterial spores are extremely tolerant to many agents and environmental conditions including radiation, desiccation, temperature, starvation and chemical agents. This natural tolerance to chemical agents allows spores to persistent for many months in key environments such as hospitals, other healthcare centers and food production facilities, where standard cleaning agents, germicides and sterilization processes do not eradicate the bacteria. In the case of food production, the presence of spores can have significant consequences ranging from simple food spoilage to the spread of food-borne pathogens and food poisoning. More recently, attention has been drawn to the risks associated with the spores of *Bacillus anthracis*, the causative agent of anthrax. The spores can be readily prepared as a dry powder that can be disseminated by numerous methods and used as a bioterrorist agent. Anthrax is considered the single most worrying bioterrorism agent (CDC Emerg. Infect. Dis., 2004, 5 (4), 552-555). This can be highlighted by the postal anthrax attacks in the United States in 2001. There were 22 confirmed infections resulting in 5 deaths with the cost of cleanup and decontamination following the attacks estimated at $1 billion.

Important spore-forming bacteria are the Gram-positive endospore-forming bacteria of the genera *Bacillus* and *Clostridium*. Examples of the genus *Bacillus* of health concern to humans include, but are not limited to, *B. anthracis* and *B. cereus*. *Bacillus anthracis* is of particular concern as the causative agent of anthrax. Anthrax infection can occur through ingestion, inhalation or cutaneous contact with *Bacillus anthracis* spores resulting in three distinct clinical forms. Cutaneous infection accounts for about 95% of all infections and is generally well controlled with the use of suitable antibiotics. Around 20% of untreated cases of cutaneous anthrax will result in death. Intestinal infection is characterized by an acute inflammation of the intestinal tract resulting in nausea, loss of appetite, vomiting, fever, abdominal pain, vomiting of blood and severe diarrhoea. Intestinal anthrax results in death in 25% to 60% of cases. The most severe form of the disease is pulmonary anthrax which is often fatal, even with aggressive and timely antibiotic administration. The ability to readily disperse anthrax spores through the air and over a wide area to induce pulmonary anthrax makes anthrax the primary bioterrorism agent.

Members of the genus *Clostridium* are Gram-positive, spore-forming, obligate anaerobes. Exemplary species causing human disease include, but are not limited to, *C. perfringens, C. tetani, C. botulinium, C. sordellii* and *C. difficile*. Clostridia are associated with diverse human diseases including tetanus, gas gangrene, botulism and pseudomembraneous colitis and can be a causative agent in food poisoning.

Of particular concern is disease caused by *Clostridium difficile*. *Clostridium difficile* causes *Clostridium difficile*-associated diseases (CDAD) and there has been a ten-fold increase in the number of cases within the last 10 years, with hyper-virulent and drug resistant strains now becoming endemic. Recent Health Protection Agency (HPA) figures show there were 55,681 cases of *C. difficile* infection in patients aged 65 years and above in England in 2006 (up 8% from the previous year). Perhaps most worrying are the cases of CDAD now being reported with no underlying antibiotic use.

*Clostridium difficile* is a commensal enteric bacterium, the levels of which are kept in check by the normal gut flora. However, the bacterium is the causative agent of *C. difficile*-associated disease (CDAD) and has been identified as the primary cause of the most serious manifestation of CDAD, pseudomembraneous colitis. CDAD is associated with a wide range of symptoms ranging from mild diarrhoea to pseudomembraneous colitis, toxic megacolon and death. The primary risk factor for the development of CDAD is the use of antibiotics disrupting the normal enteric bacterial flora causing an overgrowth of *Clostridium difficile*. Although clindamycin is the major antibiotic associated with CDAD, the disease is now associated with nearly all antibiotics including members of the fluoroquinolone, cephalosporin, macrolide, β-lactam and many others classes.

CDAD is primarily of concern in the hospital setting and is of particular concern amongst elderly patients where mortality rates are particularly high. Mortality rates in the USA have risen from 5.7 per million of population in 1999 to 23.7 per million in 2004. Colonization rates of *C. difficile* in the general population are up to 3% although hospitalization dramatically increases the rates of colonization up to 25%. Of particular concern is the emergence of new endemic strains. A particularly pertinent example is the hyper-virulent BI/NAP1 (also known as ribotype 027) strain which shows increased toxin A and B production as well as the production of additional novel binary toxins. The hyper-sporulation characteristics of strains such as BI/NAP 1 contribute significantly to the issue. Gastric acidity is part of the natural defense mechanism against ingested pathogens and any reduction in the acidity of the stomach can result in colonization of the normally sterile upper gastrointestinal tract which can result in a disturbance of the normal enteric microflora. As such, the use of gastric acid suppressive agents, such as proton pump inhibitors (PPIs) and histamine H2-receptor antagonists (H2RAs) is associated with an increased risk of *C. difficile* colonization and subsequent development of CDAD. The use of PPIs and H2RAs has previously been associated with other enteric infections such as traveller's diarrhoea, salmonellosis and cholera. It has been reported that the risk of CDAD increases with the use of gastric acid suppressive agents in both the community and hospital settings.

PPIs include, but are not limited to, omeprazole (Losec, Prilosec, Zegerid), lansoprazole (Prevacid, Zoton, Inhibitol), esomeprazole (Nexium), pantoprazole (Protonix, Somac, Pantoloc, Pantozol, Zurcal, Pan) and rabeprazole (Rabecid, Aciphex, Pariet, Rabeloc).

H2RAs include, but are not limited to, cimetidine (Tagamet), ranitidine (Zinetac, Zantac), famotidine, (Pepcidine, Pepcid), roxatidine (Roxit) and nizatidine (Tazac, Axid).

Triple therapy with PPIs or H2RAs together with a combination of two antibiotics is a recognized treatment for the eradication of *Helicobacter pylori* infections (Aliment. Pharmacol. Ther., 2001, 15(5), 613-624; Helicobacter., 2005, 10(3), 157-171). However, there are a few reports that this triple therapy regimen can lead to CDAD side effects (Am. J. Gastroenterol., 1998, 93(7), 1175-1176; J. Int. Med., 1998, 243(3), 251-253; Aliment. Pharm. Ther., 2001, 15(9), 1445-1452; Med. Sci. Monit., 2001, 7(4), 751-754). Typical antibacterials used to treat *Helicobacter pylori* infections are a combination of agents selected from, but not limited to metronidazole, amoxicillin, levofloxacin and clarithromycin—many of which are strongly associated with the development of CDAD. Current therapies are extremely limited; particularly in view of the fact nearly all antibiotic classes are associated with causing the disease. The only FDA approved drug for treatment of CDAD is vancomycin although metronidazole is also extensively used. Widespread vancomycin use for the treatment of CDAD is of concern due to its bacteriostatic action against clostridia, relatively high cost and the possible selection of resistant *C. difficile* strains as well as other bacteria (particularly *Enterococcus* spp.). A key issue with both metronidazole and vancomycin is the high relapse rate with at least 20% of patients experiencing at least one recurrent episode. Relapse is proposed to occur due to the inability to eradicate the *clostridium* spores during therapy resulting in subsequent outgrowth to a pathogenic state. This inability to control spore formation allows for continued contamination of the hospital environment. As such, agents able to eradicate vegetative cells and control endospores would be of significant advantage.

The primary therapy option for the treatment of CDAD is discontinuation of any current antimicrobial treatment followed by appropriate use of either vancomycin or metronidazole. Both agents are usually administered orally although metronidazole may also be administered intravenously and in severe cases, vancomycin may also be administered via numerous other routes including intracolonic, through nasal gastric tube or as a vancomycin-retention enema. Additional antibiotics agents that have been reported to be used in the treatment of CDAD include fusidic acid, rifamycin and its analogues, teicoplanin and bacitracin although none show particular efficacy over vancomycin or metronidazole. In addition to halting any offending antibacterial treatment, the use of antiperistaltic agents, opiates, or loperamide should be avoided since they can reduce clearance of the *C. difficile* toxins and exacerbate toxin-mediated colonic injury.

Alternative therapies, used as stand-alone agents or in conjunction with antibacterials, are aimed at either trying to re-establish the native gut microorganism population, reducing the levels of *C. difficile* toxins or stimulating the immune system. Thus, alternative CDAD therapies include provision of *Saccharomyces boulardii* or *Lactobacillus acidophilus* in conjunction with antibiotics, faecal transplantation and in severe cases where all other therapy options have failed, surgery. Although rates of colectomy are low (up to 3% of cases) it is associated with high mortality rates (up to 60%).

As such, there is a pressing need for new and effective agents to treat diseases associated with spore forming bacteria, particularly those caused by members of the genera *Clostridium* and *Bacillus* and in particular disease associated with *Clostridium difficile* infection. This need is particularly acute in the light of the refractory nature of *Clostridium difficile* to many broad spectrum antibiotics (including β-lactam and quinolone antibiotics) and the frequency with which resistance emerges.

Among the Prior Art relevant to addressing issues with *Clostridium difficile* are:

WO2007056330, WO2003105846 and WO2002060879 disclose various 2-amino benzimidazoles as antibacterial agents.

WO2007148093 discloses various 2-amino benzothiazoles as antibacterial agents.

WO2006076009, WO2004041209 and Bowser et al. (Bioorg. Med. Chem. Lett., 2007, 17, 5652-5655) disclose various substituted benzimidazole compounds useful as anti-infectives that decrease resistance, virulence, or growth of microbes. The compounds are said not to exhibit intrinsic antimicrobial activity in vitro.

U.S. Pat. No. 5,824,698 discloses various dibenzimidazoles as broad-spectrum antibiotics, disclosing activity against both Gram-negative and Gram-positive bacteria, including *Staphylococcus* spp. and *Enterococcus* spp. However, this document does not disclose activity against anaerobic spore-forming bacteria and in particular does not disclose activity against any *Clostridium* spp. (including *C. difficile*).

US Published Patent Application Document No. 20070112048 (Bavari) discloses various bi- and triarylimidazolidines and bi- and triarylamidines as broad-spectrum antibiotics, disclosing activity against both Gram-negative and Gram-positive bacteria, including *Staphylococcus* spp., *Enterococcus* spp. and *Clostridium* spp. However, this document does not disclose compounds of general formula (I) as described herein.

It has been found that certain imidazoles and or their derivatives are capable of inhibiting the growth of *Clostridium difficile* (George, 1979), MRSA (Lee & Kim, 1999) and/or VISA, VRSA and VRE. However, the identification of compounds that act synergistically with these drugs (the imidazoles) means that lower concentrations of original drug may be used (thus reducing the undesirable side effects of the imidazoles) and prolonging the life of the drug treatment (e.g. a synergistic combination of two drugs will require resistance to develop in both components before the combination becomes ineffective). If the spontaneous rate of resistance development in an organism is $10^8$, the development of resistance to the combination of two compounds will be approximately $10^{64}$, therefore the risk of resistance developing is dramatically lower.

US Published Patent Application Document No. 20110229583 (Tran) describes that a medicinal drug is administered to a person for treating a medical condition of the person or/and for preventing the person from contracting the medical condition. The medical condition can be a bacterial infection, a eukaryotic infection, a prion-caused infection, a non-pathogenic inflammation, and, insofar as not covered by any of these four types of the medical condition, a fungal infection, a spore-caused infection, and a parasitic infection. A medicinal drug is similarly administered non-topically to a person for treating a virus-caused medical condition of the person or/and for preventing the person from contracting the virus-caused medical condition. The medicinal drug is typically formed at least partially with salt of peroxymonosulfuric acid, preferably potassium hydrogen peroxymonosulfate.

US Published Patent Application Document No. 20110183360 (Rajagapol) describes an isolated antibody that binds to putative N-acetylmuramoyl-L-alanine amidase protein of *Clostridium difficile* strain 630 having SEQ ID NO: 5 or a fragment of the putative N-acetylmuramoyl-L-alanine amidase protein. In some embodiments, the isolated antibody binds to a fragment of the putative N-acetylmuramoyl-L-alanine amidase protein including amino acid residues 294 to 393. In some embodiments, the isolated antibody binds to a fragment of the putative N-acetylmuramoyl-L-alanine amidase protein including amino acid residues 582 to 596. In some embodiments, the isolated antibody binds to a fragment of the putative N-acetylmuramoyl-L-alanine amidase protein including amino acid residues 64 to 78.

Published U.S. Patent Application Document No, 20110086797 (Dworkin) describes compositions and methods for treating bacterial infections. It is demonstrated herein that bacteria cell wall materials stimulate germination of spores of Gram-positive bacteria, and that such activity requires Ser/Thr kinase PrkC. By modulating one or both, spores (which can be antibiotic resistant) can be stimulated or inhibited from germination, which can be exploited in various methods of therapeutic treatment. Also provided is a method of modulating germination of a spore of a Gram-positive bacterium. Also provided is a method of decontaminating an environment.

Published U.S. Patent Application Document No. 20120020950 (Davis) describes novel compounds of a specific formula (I), which are of use in the treatment of bacterial diseases and infections, to compositions containing those compounds and to methods of treating bacterial diseases and infections using the compounds. In particular, the compounds are useful for the treatment of infection with, and diseases caused by, *Clostridium difficile*.

Published U.S. Patent Application Document No. 20080254010 (Sasser) discloses treating a patient infected with spore-forming bacteria by administering to the patient an antibiotic and a spore germinant in amounts and for durations effective for treating said patient. Among the spore germinants is listed bile salts, and specifically taurocholate.

Published U.S. Patent Application Document No. 20110280847 (Sorg) describes methods and treatments for inhibiting *Clostridium difficile* spore germination and outgrowth using chemical means. Among the chemical means are specific compounds derivatized from specific bile salts defined by structural formulae.

SUMMARY OF THE INVENTION

A method of reducing risk of developing *Clostridium difficile*-associated disease or reducing existing *Clostridium difficile*-associated disease in a mammalian subject receiving antibiotic therapy, comprising administering to a mammalian subject an effective amount of a compound derived from taurocholate. The compound derived from taurocholate preferably has the central core structure of the formula:

The method may include parallel or adjacent or preceding or subsequent treatment with an antibiotic, with the mammalian subject already receiving antibiotic therapy and at risk of developing *C. difficile*-associated disease.

BRIEF DESCRIPTION OF THE FIGURES

FIG. 1. Germination kinetic graphs showing agonistic and antagonistic behavior of molecules with *C. difficile* spores.

FIG. 2. Amino acids assessed for activation or inhibition of glycine-mediated germination in *C. difficile* spores.

FIG. 3. Comparison of amino acids as agonists of *C. difficile* spore germination.

FIG. 4. Germination kinetic graph showing behavior of *C. difficile* spores and germinants in buffer and complex media.

FIG. 5. A chart of taurocholate analogs assessed for activation or inhibition of taurocholate-mediated germination in *C. difficile* spores.

FIG. 6 is a generic structural formula showing the central core and ring positions on a taurocholate molecule.

FIG. 7 is a more specific central core nucleus showing at least the major positions on the taurocholate central core on which substituents are placed within the scope of the present technology.

FIG. 8 is Table 3. Effect of taurocholate hydroxyl groups on *C. difficile* spore germination.

FIG. 9 is Table 4. Effect of the taurocholate side chain on *C. difficile* spore germination.

FIG. 10 is a graph evidencing that mice treated with CamSA or chenodeoxycholate show no weight changes with particular treatments.

FIG. 11 shows graphic results of protection of mice from CDI by different bile salts. The data is shown in a Kaplan-Meier survival plot for treated *C. difficile* infected mice.

FIG. 12 shown graphic representations of signs of severity for *C. difficile* infected animals treated with different bile salts.

FIG. 13 graphically shows that CamSA does not affect vegetative bacterial growth.

FIG. 14 graphically shows that CamSA is not toxic to mammalian cells.

FIG. 15 graphically shows distribution of *C. difficile* spores in the GI tract of CamSA-treated animals. The stomach (St), duodenum (Du), jejunum (Je), and ileum (Il) showed negligible amounts of spores compared to the cecum (Ce) and colon (Co).

FIG. 16 is graphic evidence that CamSA protects mice from CDI.

FIG. 17 is a graphic representation of data showing that *C. difficile* spores accumulate in the cecum, colon, and feces of CamSA-treated animals.

FIG. 18 is a time line model for CDI onset in mice. *C. difficile* spores (black circles) that are ingested by the host.

FIG. 19 is a graphic representation of the stability of CamSA and taurocholate towards bile salt hydrolases.

FIG. 20 is a graphic representation of the cytotoxicity of CamSA.

FIG. 21 is a graphic representation of inhibition of *C. difficile* toxin production by CamSA treatment.

FIG. 22 is a graphic representation that CDI is established between 6 and 9 hours post-infection

DETAILED DESCRIPTION OF THE INVENTION

Novel compounds and a method of using those novel compounds and even known compounds in a treatment for mammalian subjects. The treatment may affect (reduce) the rate of germination of spores that form *Clostridium difficile* and may reduce risk of developing *Clostridium difficile*-associated disease or reducing existing *Clostridium difficile*-associated disease in a mammalian subject receiving antibiotic therapy, comprising administering to a mammalian subject an effective amount of a compound derived from taurocholate.

The term "central core structure" is intended to mean that pharmacologically acceptable dertivatives of the core structure shown in the formula are included within the scope of that description, whether in the specific or the claims. Only where reference is specific to a formula, without expansive legal or technical terms is a narrower construction of the scope of a formula intended.

The methods of the present technology and the included compounds may be approximately generally include a method of treating a patient to reduce risk of developing *Clostridium difficile*-associated disease or reducing existing *Clostridium difficile*-associated disease in a mammalian subject. Steps may include administering to a mammalian subject an effective amount of a germination-inhibiting compound derived from taurocholate. The compound derived from taurocholate may, for example, have a central core structure of the formula:

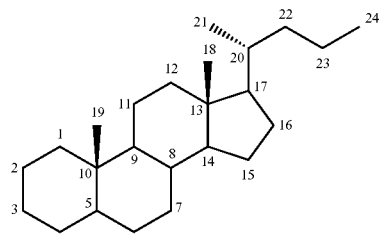

The compound derived from taurocholate may be, for example, a compound within the non-limiting, exemplary formula:

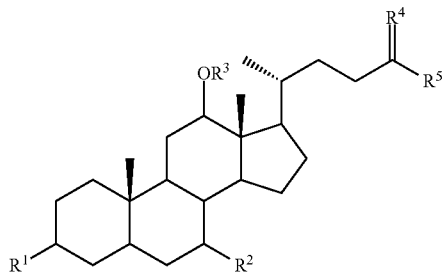

wherein $R^1$ is selected from the group consisting of hydrogen, lower alkyl of $C_1$ to $C_6$, amines, halogen, cyano, hydroxyl, carboxylic acid groups and substituted lower alkyl of $C_1$ to $C_6$, wherein the substituents are selected from the group consisting of halogen, cyano, hydroxyl and the like;

$R^2$ is selected from the group consisting of hydrogen, lower alkyl of $C_1$ to $C_6$, halogen, cyano, amines, hydroxyl, carboxylic acid groups and substituted lower alkyl of $C_1$ to $C_6$, wherein the substituents are selected from the group consisting of halogen, cyano, hydroxyl and the like.

$R^3$ is selected from the group consisting of hydrogen, lower alkyl of $C_1$ to $C_6$, halogen, cyano, hydrogen, carboxylic acid groups and substituted lower alkyl of $C_1$ to $C_6$, wherein the substituents on the alkyl groups are selected from the group consisting of halogen, cyano, hydroxyl;

$R^4$ is selected from the group consisting of O and S; and $R^5$ is selected from the group consisting of
1) $NH(CH_2)_2SO_3H$
2) $NHCH_2SO_3H$
3) $NH(CH_2)_3SO_3H$
4) $NH(p\text{-}(C_6H_4))SO_3H$
5) $NH(o\text{-}(C_6H_4))SO_3H$
6) $NH(m\text{-}(C_6H_4))SO_3H$
7) $NH(CH_2)_2SO_2H$
8) $NHCH_2CO_2H$
9) $NH(CH_2)_2CO_2H$
10) $NH(CH_2)_2CONH(CH_2)_2CO_2H$
11) $NH(CH_2)_3CO_2H$
12) $NH(CH_2)_3CONH(CH_2)_3CO_2H$
13) $O(CH_2)_2SO_3H$

| Compound No. | Modifications to taurocholate side chain | $EC_{50}{}^a$ (stdev) mM | $IC_{50}{}^b$ (stdev) mM |
|---|---|---|---|
| 14 | $NH(CH_2)_4COOH$ | NA | 5.3 (0.24) |
| 15 | $NH(CH_2)_4CONH(CH_2)_4COOH$ | NA | NA |
| 16 | $NH(CH_2)_5COOH$ | NA | 2.3 (0.075) |
| 17 | $NH(CH_2)_5CONH(CH_2)_5COOH$ | NA | NA |
| 18 | $NH(CH_2)_2OSO_3H$ | NA | NA |
| 19 | $S(CH_2)_2SO_3H$ | NA | NA |
| 20 | $NHCH_2PO_3H$ | NA | NA |
| 21 | $NHC_6H_5$ | NA | 0.27 (0.070) |
| 22 | $NHC_5H_4N$ | NA | NA |
| 23 | $NH(m\text{-}(C_6H_4))COOH$ | NA | 3.1 (0.78) |
| 24 | $NH(o\text{-}(C_6H_4))COOH$ | NA | NA |
| 25 | $NH(p\text{-}(C_6H_4))COOH$ | NA | 1.4 (0.11) |
| 26 | $NH(m\text{-}(C_6H_8))COOH$ | NA | 0.47 (0.069) |
| 27 | $NH(m\text{-}(C_6H_4))COOCH_3$ | NA | NA |
| 28 | $NH(m\text{-}(C_6H_4))OPO_3H_2$ | NA | NA |
| 29 | $NH(m\text{-}(C_6H_4))OH$ | NA | NA |
| 30 | $NH(o\text{-}(C_6H_4))OH$ | NA | NA |
| 31 | $NH(m\text{-}(C_6H_4))SH$ | NA | NA |
| 32 | $NH(p\text{-}(C_6H_4))SH$ | NA | NA |

-continued

| | | EC50 (stdev) mM | IC50 (stdev) mM |
|---|---|---|---|
| 33 | NH(m-($C_6H_4$))$SCH_3$ | NA | NA |
| 34 | NH(m-($C_6H_4$))$NH_2$ | NA | 0.53 (0.022) |
| 35 | NH(m-($C_6H_4$))$CH_3$ | NA | NA |
| 36 | NH(o-$CH_3$—m-($C_6H_4$)$SO_3H$ | NA | NA |
| 37 | NH(o-$OCH_3$—m-($C_6H_4$)$SO_3H$ | 4.6 (0.34) | NA |
| 38 | NH(o-$CH_3$—m-($C_6H_4$)COOH | 16 (0.90) | NA |
| 39 | NH(p-$CH_3$—m-($C_6H_4$)COOH | NA | 11 (0.025) |
| 40 | NH(o,p-($CH_3$)$_2$—m-($C_6H_4$)$SO_3H$ | NA | 5.6 (0.042) |
| 41 | NH(p,m-($CH_3$)$_2$—m-($C_6H_4$)$SO_3H$ | NA | 1.1 (0.098) |
| 42 | $NCH_3$(m-($C_6H_4$)$SO_3H$ | 5.4 (0.10) | NA |
| 43 | $NH_2$(m-($C_6H_4$)$SO_3H$ | NA | NA |
| 44 | $NHCH_3$(m-($C_6H_4$)$SO_3H$ | NA | NA |
| 45 | NH(1-$C_{10}H_8$) | NA | NA |
| 46 | NH(2-$C_{10}H_8$) | NA | NA |
| 47 | NH($C_{14}H_{10}$) | NA | NA |
| 48 | NH($C_{16}H_{10}$) | NA | NA |
| 49 | NH($C_{10}H_8$)-3-OH | NA | NA |
| 50 | NH($C_{10}H_8$)-1-$SO_3H$ | NA | NA |
| 52 | NH($C_{10}H_8$)-1-$CO_2H$ | NA | NA |
| 53 | NH($C_{10}H_8$)-5-$CO_2H$ | 1.3 (0.19) | NA |
| 54 | NH($C_{10}H_8$)-3-OH-5-$SO_3H$ | NA | NA |
| 55 | NH($C_{10}H_8$)-1,6-$SO_3H$ | NA | NA |
| 56 | NH($C_{10}H_8$)-2,6-$SO_3H$ | 5.7 (0.26) | NA |
| 57 | $NH_2$($C_{10}H_8$)-1,5-$SO_3H$ | NA | NA |

| Compound No. | Modifications to taurochenodeoxycholate side chain | EC50 (stdev) mM | IC50 (stdev) mM |
|---|---|---|---|
| 58 | $NHCH_2SO_3H$ | 0.31 (0.023) | NA |
| 59 | NH($CH_2$)$_2$$SO_2H$ | NA | 5.3 (0.20) |
| 60 | NH($CH_2$)$_2$COOH | NA | 3.9 (0.80) |
| 61 | NH($CH_2$)$_4$COOH | NA | 0.64 (0.19) |
| 62 | NH($CH_2$)$_4$CONH($CH_2$)$_4$COOH | NA | 1.9 (0.78) |
| 63 | NH($CH_2$)$_5$COOH | NA | 1.1 (0.23) |
| 64 | NH($CH_2$)$_5$CONH($CH_2$)$_5$COOH | NA | 8.6 (0.38) |
| 65 | NH(m-($C_6H_4$))$SO_3H$ | NA | 6.5 (0.20) |
| 66 | $NHC_6H_5$ | NA | NA |
| 67 | NH(m-($C_6H_4$))COOH | NA | 0.93 (0.12) |
| 68 | NH(p-($C_6H_4$))COOH | NA | NA |
| 69 | NH(m-($C_6H_8$))COOH | 7.4 (0.65) | NA |
| 70 | NH(m-($C_6H_4$))$NH_2$ | NA | NA |
| 71 | NH(p-$CH_3$—m-($C_6H_4$)COOH | NA | 0.092 (0.014) |
| 72 | NH(o,p-($CH_3$)$_2$—m-($C_6H_4$)$SO_3H$ | NA | 0.92 (0.16) |
| 73 | NH(p,m-($CH_3$)$_2$—m-($C_6H_4$)$SO_3H$ | NA | 0.75 (0.077) |
| 74 | NH($C_{10}H_8$)-2,6-$SO_3H$ | NA | 12 (0.48) |

| Compound No. | Modifications to cholic acid | EC50 (stdev) mM | IC50 (stdev) mM |
|---|---|---|---|
| 75 | Shorter alkyl chain | NA | 6.3 (0.0070) |
| 76 | Alcohol side chain | NA | 0.33 (0.0072) |
| 77 | Methyl ester side chain | NA | 0.059 (0.0079) |
| 78 | Methyl ester side chain - shorter alkyl chain by 1 carbon | NA | 0.15 (0.063) |
| 79 | Methyl ester side chain - shorter alkyl chain by 2 carbon | NA | 0.66 (0.10) |
| 80 | Ethyl ester side chain | NA | 0.0082 (0.00050) |
| 81 | Methoxylated hydroxyl groups | NA | NA |
| 82 | Hydroxyls at 3 ($\alpha$) and 12 ($\alpha$) | NA | 0.19 (0.025) |
| 83 | Hydroxyls at 3 ($\alpha$) and 12 ($\beta$) | NA | NA |
| 84 | Hydroxyls at 3 ($\beta$) and 12 ($\alpha$) | NA | 0.78 (0.073) |
| 85 | Methyl ester with hydroxyls at 3 ($\alpha$) and 12($\alpha$) | NA | 0.097 (0.068) |
| 86 | Methyl ester with hydroxyls at 3 ($\alpha$) and 12 ($\beta$) | NA | 0.095 (0.0012) |
| 87 | Hydroxyls at 3 ($\alpha$) and 6 ($\alpha$) | NA | 1.24 (0.11) |
| 88 | Methyl ester with hydroxyls at 3 ($\alpha$) and 6 ($\alpha$) | NA | 0.037 (0.021) |
| 89 | Alcohol with hydroxyl at 3 ($\alpha$) | NA | NA |
| 90 | Methyl ester with hydroxyl at 12 ($\alpha$) | NA | 0.37 (0.051) |
| 91 | Methyl ester with hydroxyl at 3 ($\beta$) | NA | 1.3 (0.54) |

[a] *C. difficile* spores were individually treated with 6 mM glycine and bile salt analogs. Standard deviations are shown in parentheses.
[b] *C. difficile* spores were incubated with bile salt analogs for 15 min prior to the addition of 6 mM taurocholate and 12 mM glycine. Standard deviations are shown in parentheses.
[c] NA, no change in absorbance after 90 minutes under the conditions tested thus no statistics could be performed.

The present technology evidences that inhibiting *Clostridium difficile* spore germination serves as a prophylactic approach to prevent *Clostridium difficile*-associated diseases (CDAD) or *Clostridium difficile* infection (CDI). CDI is the major cause of antibiotic-associated diarrhea. In the US, there are approximately 500,000 CDI cases annually, with a mortality rate >2.5%. The annual CDI-associated costs have been estimated at $3.2 billion. CDI responds poorly to most antibiotics since its onset typically occurs while patients are receiving antimicrobial therapy. Indeed, only metronidazole and vancomycin are currently used to treat CDI. The incidence of CDI is complicated by the appearance of highly resistant and hypervirulent strains.

The infectious form of *C. difficile* is the spore, a dormant and resistant structure formed from vegetative cells during nutrient deprivation. *C. difficile* spores revert to toxin-producing bacteria (a process called germination) in nutrient-rich environments. Germination of *C. difficile* spores in the GI tract of hospitalized patients is the first committed step in CDI. We propose that compounds able to curtail spore germination could also prevent CDI establishment. Anti-germination compounds could be used to supplement antibiotic treatments of hospitalized patients. Once the antibiotic regime is completed, re-establishment of the normal gut flora will prevent *C. difficile* colonization and anti-germination therapy can also be stopped. The present technology evidences that *C. difficile* spores bind the germinants taurocholate (a bile salt) and glycine through a complex mechanism. We also found that a synthetic taurocholate analog with an m-aminobenzenesulfonic acid side chain (CamSA) is an efficient inhibitor of *C. difficile* spore germination. CamSA binds to *C. difficile* spores approximately 1,000-fold better than the natural taurocholate germinant. More recently, we found that CamSA (an anti-germinant) prevents CDAD in a mouse model, while taurocholate itself (a germinant) worsen CDI symptoms. Even more, CamSA does not show acute toxicity even at 300 mg/Kg and is stable to the GI tract environment.

The transformation process from a dormant spore to a fully vegetative bacterium is the initial step in CDI infections. New methods to impede spore germination would preclude the production of toxins and antibiotic-resistant factors, thus reducing morbidity and mortality. Targeting spore germination to prevent CDI is an approach that could complement future antibiotic treatments. Since the first step in the establishment of CDI is the germination of *C. difficile* spores in the microflora-depleted gut of hospitalized patients, anti-germination compounds (e.g. CamSA and CamSA analogs) could be used in combination therapies to supplement antibiotic treatments in immune-compromised patients. Once the antibiotic regime is completed, re-establishment of the normal gut flora will prevent *C. difficile* spore germination and anti-germination therapy can also be stopped.

The method may include parallel or adjacent or preceding or subsequent treatment with an antibiotic, with the mammalian subject already receiving antibiotic therapy and at risk of developing *C. difficile*-associated disease.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from trauma, injury, surgery, radiological ablation, poisoning or nutritional deficiencies.

As used herein, the term "bacterial disease" refers to any disease that involves (e.g. is caused, exacerbated, associated with or characterized by the presence of) a bacterium residing and/or replicating in the body and/or cells of a subject. The term therefore includes diseases caused or exacerbated by bacterial toxins (which may also be referred to herein as "bacterial intoxication").

As used herein, the term *Clostridium difficile*-associated disease (CDAD) or *Clostridium difficile* infection (CDI) is used to define any disease that involves (e.g. is caused, exacerbated, associated with or characterized by the presence of) *Clostridium difficile* residing and/or replicating in the body of a subject. Thus, the term covers any disease, disorder, pathology, symptom, clinical condition or syndrome in which bacteria of the species *Clostridium difficile* act as aetiological agents or in which infection with one or more strains of *Clostridium difficile* is implicated, detected or involved. The term therefore includes the various forms of colitis, pseudomembranous colitis, diarrhea and antibiotic-associated disease.

As used herein, the term "bacterial infection" is used to define a condition in which a subject is infected with a bacterium. The infection may be symptomatic or asymptomatic. In the latter case, the subject may be identified as infected on the basis of various tests, including for example biochemical tests, serological tests, microbiological culture and/or microscopy.

The terms bacteriostatic and bacteriocidal are terms of art used to define the ability to prevent (or reduce the rate of) bacterial growth and to mediate (directly or indirectly) the cellular destruction of bacterial cells, respectively. The terms are not mutually exclusive, and many agents exert both bacteriostatic and bacteriocidal effects (in some cases in a dose-specific or target-specific manner). In general, bacteriocidal agents yield better therapeutic results and are preferred.

As used herein, the term "broad spectrum antibiotic" defines an agent which is bacteriocidal and/or bacteriostatic for a range of bacteria including both Gram-positive and Gram-negative bacteria.

The "term multi-drug resistant" (MDR) as applied herein to a bacterium defines a bacterium which is resistant to two or more classes of antibiotics including, but not limited to, antibiotics selected from penicillin, methicillin, quinolone, macrolide and/or vancomycin.

As used herein, the term "treatment" or "treating" refers to an intervention (e.g., the administration of an agent to a subject) which cures, ameliorates, stabilizes or lessens the symptoms of a disease or removes (or lessens the impact of) its cause(s) (for example, the causative bacterium). In this case, the term is used synonymously with the term "therapy." Thus, the treatment of infection according to the invention may be characterized by the (direct or indirect) bacteriostatic and/or bacteriocidal action of the compounds of the invention.

Additionally, the terms "treatment" or "treating" refers to an intervention (e.g., the administration of an agent to a subject) which prevents, slows or delays the onset or progression of a disease or reduces (or eradicates) its incidence within a treated population. In this case, the term treatment is used synonymously with the term "prophylaxis."

The term "subject" (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and so on. In preferred embodiments, the subject is a human, for example an infant human.

The term Gram-positive bacterium is a term of art defining a particular class of bacteria that are grouped together on the basis of certain cell wall staining characteristics.

The term low G+C Gram-positive bacterium is a term of art defining a particular subclass class of evolutionarily related bacteria within the Gram-positives on the basis of the composition of the bases in the DNA. The subclass includes *Streptococcus* spp., *Staphylococcus* spp., *Listeria* spp., *Bacillus* spp., *Clostridium* spp., *Enterococcus* spp. and *Lactobacillus* spp.

The term "minimum inhibitory concentration" or "MIC" defines the lowest concentration of a test compound that is needed to inhibit germination of a spore in vitro or in vivo. A common method for determining the MIC of an antibiotic is to prepare several tubes containing serial dilutions of the test compound that are then inoculated with the bacterial isolate of interest. Following incubation at appropriate atmosphere and temperature, the MIC of an antibiotic can be determined from the tube with the lowest concentration that shows no turbidity.

As used herein, the term "combination", as applied to two or more compounds and/or agents (also referred to herein as the components), is intended to define material in which the two or more compounds/agents are associated. The terms "combined" and "combining" in this context are to be interpreted accordingly. The association of the two or more compounds/agents in a combination may be physical or non-physical. Examples of physically associated combined compounds/agents include: compositions (e.g. unitary formulations) comprising the two or more compounds/agents in admixture (for example within the same unit dose); compositions comprising material in which the two or more compounds/agents are chemically/physicochemically linked (for example by crosslinking, molecular agglomeration or binding to a common vehicle moiety); compositions comprising material in which the two or more compounds/agents are chemically/physicochemically co-packaged (for example, disposed on or within lipid vesicles, particles (e.g. micro- or nanoparticles) or emulsion droplets); pharmaceutical kits, pharmaceutical packs or patient packs in which the two or more compounds/agents are co-packaged or co-presented (e.g. as part of an array of unit doses).

Examples of non-physically associated combined compounds/agents include:

material (e.g. a non-unitary formulation) comprising at least one of the two or more compounds/agents together with instructions for the extemporaneous association of the at least one compound/agent to form a physical association of the two or more compounds/agents;

material (e.g. a non-unitary formulation) comprising at least one of the two or more compounds/agents together with instructions for combination therapy with the two or more compounds/agents;

material comprising at least one of the two or more compounds/agents together with instructions for administration to a patient population in which the other(s) of the two or more compounds/agents have been (or are being) administered;

material comprising at least one of the two or more compounds/agents in an amount or in a form which is specifically adapted for use in combination with the other(s) of the two or more compounds/agents.

As used herein, the term "combination therapy" is intended to define therapies which comprise the use of a combination of two or more compounds/agents (as defined above) whether both are germination suppressants or one is an antimicrobial, such as an antibiotic or antifungal agent. Thus, references to "combination therapy," "combinations" and the use of compounds/agents "in combination" in this application may refer to compounds/agents that are administered as part of the same overall treatment regimen. As such, the posology of each of the two or more compounds/agents may differ: each may be administered at the same time or at different times. It will therefore be appreciated that the compounds/agents of the combination may be administered sequentially (e.g. before or after) or simultaneously, either in the same pharmaceutical formulation (i.e. together), or in different pharmaceutical formulations (i.e. separately). Simultaneously in the same formulation is as a unitary formulation, whereas simultaneously in different pharmaceutical formulations is non-unitary. The posologies of each of the two or more compounds/agents in a combination therapy may also differ with respect to the route of administration.

As used herein, an effective amount or a therapeutically effective amount of a compound defines an amount that can be administered to a subject without excessive toxicity, irritation, allergic response, or other problem or complication, commensurate with a reasonable benefit/risk ratio, but one that is sufficient to provide the desired effect, e.g., the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure.

As used herein, a "prophylactically effective amount" refers to an amount effective, at dosages, at particular sites and for periods of time necessary, to achieve a prophylactic result or the desired prophylactic result. Typically, since a prophylactic dose is used in subjects prior to or at an earlier stage of disease, the prophylactically effective amount will be less than the therapeutically effective amount.

The term "efficacious" includes advantageous effects such as additivity, synergism, reduced side effects, reduced toxicity or improved performance or activity. Advantageously, an efficacious effect may allow for lower doses of each or either component to be administered to a patient, thereby decreasing the toxicity, whilst producing and/or maintaining the same therapeutic effect. A synergistic effect in the present context refers to a therapeutic effect produced by the combination which is larger than the sum of the therapeutic effects of the components of the combination when presented individually. An additive effect in the present context refers to a therapeutic effect produced by the combination which is larger than the therapeutic effect of any of the components of the combination when presented individually.

The term "ancillary compound" (or "ancillary agent") as used herein is intended to define any compound which yields an efficacious combination (as herein defined) when combined with a compound of the invention. The ancillary compound may therefore act as an adjunct to the compound of the invention, or may otherwise contribute to the efficacy of the combination (for example, by producing a synergistic or additive effect or by potentiating the activity of the compound of the invention).

The term "adjunctive" as applied to the use of the compounds and combinations of the invention in therapy or prophylaxis defines uses in which the materials are administered together with one or more other drugs, interventions, regimens or treatments (such as surgery and/or irradiation). Such adjunctive therapies may comprise the concurrent, separate or sequential administration/application of the materials of the invention and the other treatment(s). Thus, in some embodiments, adjunctive use of the materials of the invention is reflected in the formulation of the pharmaceutical compositions of the invention. For example, adjunctive use may be reflected in a specific unit dosage or in formulations in which the compound of the invention is present in admixture with the other drug(s) with which it is to be used adjunctively (or else physically associated with the other drug(s) within a single unit dose). In other embodiments, adjunctive use of the compounds or compositions of the invention may be reflected in the composition of the pharmaceutical kits of the invention, wherein the compound of the invention is co-packaged (e.g., as part of an array of unit doses) with the other drug(s) with which it is to be used adjunctively. In yet other embodiments, adjunctive use of the compounds of the invention may be reflected in the content of the information and/or instructions co-packaged with the compound relating to formulation and/or posology.

The term pharmaceutically acceptable derivative as applied to the compounds of the invention define compounds which are obtained (or obtainable) by chemical derivatization of the parent compounds of the invention. The pharmaceutically acceptable derivatives are therefore suitable for administration to or use in contact with mammalian tissues without undue toxicity, irritation or allergic response (i.e., commensurate with a reasonable benefit/risk ratio). Preferred derivatives are those obtained (or obtainable) by alkylation, esterification or acylation of the parent compounds of the invention. The derivatives may be active per se, or may be inactive until processed in vivo. In the latter case, the derivatives of the invention act as prodrugs. Particularly preferred prodrugs are ester derivatives which are esterified at one or more of the free hydroxyls and which are activated by hydrolysis in vivo. Other preferred prodrugs are covalently bonded compounds which release the active parent drug according to general formula (I) after cleavage of the covalent bond(s) in vivo.

The pharmaceutically acceptable derivatives of the invention retain some or all of the activity of the parent compound. In some cases, the activity is increased by derivatization. Derivatization may also augment other biological activities of the compound, for example bioavailability.

The term pharmaceutically acceptable salt as applied to the compounds of the invention defines any non-toxic organic or inorganic acid addition salt of the free base compound which is suitable for use in contact with mammalian tissues without undue toxicity, irritation, allergic response and which are commensurate with a reasonable benefit/risk ratio. Suitable pharmaceutically acceptable salts are well known in the art. Examples are the salts with inorganic acids (for example hydrochloric, hydrobromic, sulfuric and phosphoric acids), organic carboxylic acids (for example acetic, propionic, glycolic, lactic, pyruvic, malonic, succinic, fumaric, malic, tartaric, citric, ascorbic, maleic, hydroxymaleic, dihydroxymaleic, benzoic, phenylacetic, 4-aminobenzoic, 4-hydroxybenzoic, anthranilic, cinnamic, salicylic, 2-phenoxybenzoic, 2-acetoxybenzoic and mandelic acid) and organic sulfonic acids (for example methanesulfonic acid and p-toluenesulfonic acid). The compounds of the invention may also be converted into salts by reaction with an alkali metal halide, for example sodium chloride, sodium iodide or lithium iodide. Preferably, the compounds of the invention are converted into their salts by reaction with a stoichiometric amount of sodium chloride in the presence of a solvent such as acetone.

These salts and the free base compounds can exist in either a hydrated or a substantially anhydrous form. Crystalline forms of the compounds of the invention are also contemplated and in general the acid addition salts of the compounds of the invention are crystalline materials which are soluble in water and various hydrophilic organic solvents and which in comparison to their free base forms, demonstrate higher melting points and an increased solubility.

The term pharmaceutically acceptable solvate as applied to the compounds of the invention defines any pharmaceutically acceptable solvate form of a specified compound that retains the biological effectiveness of such compound. Examples of solvates include compounds of the invention in combination with water (hydrates), isopropanol, ethanol, methanol, dimethyl sulfoxide, ethyl acetate, acetic acid, ethanolamine, or acetone. Also included are miscible formulations of solvate mixtures such as a compound of the invention in combination with an acetone and ethanol mixture. In a preferred embodiment, the solvate includes a compound of the invention in combination with about 20% ethanol and about 80% acetone. Thus, the structural formulae include compounds having the indicated structure, including the hydrated as well as the non-hydrated forms.

The term pharmaceutically acceptable prodrug as applied to the compounds of the invention defines any pharmaceutically acceptable compound that may be converted under physiological conditions or by solvolysis to the specified compound, to a pharmaceutically acceptable salt of such compound or to a compound that shares at least some of the antibacterial activity of the specified compound (e.g. exhibiting activity against *Clostridium difficile*).

The term pharmaceutically acceptable metabolite as applied to the compounds of the invention defines a pharmacologically active product produced through metabolism in the body of the specified compound or salt thereof.

Prodrugs and active metabolites of the compounds of the invention may be identified using routine techniques known in the art (see for example, Bertolini et al., J. Med. Chem., 1997, 40, 2011-2016).

The term pharmaceutically acceptable complex as applied to the compounds of the invention defines compounds or compositions in which the compound of the invention forms a component part. Thus, the complexes of the invention include derivatives in which the compound of the invention is physically associated (e.g. by covalent or non-covalent bonding) to another moiety or moieties. The term therefore includes multimeric forms of the compounds of the invention. Such multimers may be generated by linking or placing multiple copies of a compound of the invention in close proximity to each other (e.g. via a scaffolding or carrier moiety).

FIG. 6 is a generic structural formula showing the central core and ring positions on a taurocholate molecule.

FIG. 7 is a more specific central core nucleus showing at least the major positions on the taurocholate central core on which substituents are placed within the scope of the present technology.

Specific chemical names for compounds within these groups of constituents include at least the following:

Taurocholate $NH(CH_2)_2SO_3H$
2-[(3α,7α,12α-trihydroxy-24-oxo-5β-cholan-24-yl)amino]ethanesulfonic acid
$NHCH_2SO_3H$
1-[(3α,7α,12α-trihydroxy-24-oxo-5β-cholan-24-yl)amino]methanesulfonic acid
$NH(CH_2)_3SO_3H$
3-[(3α,7α,12α-trihydroxy-24-oxo-5β-cholan-24-yl)amino]propanesulfonic acid
$NH(p\text{-}(C_6H_4))SO_3H$
4-[(3α,7α,12α-trihydroxy-24-oxo-5β-cholan-24-yl)amino]benzenesulfonic acid
$NH(o\text{-}(C_6H_4))SO_3H$
1-[(3α,7α,12α-Trihydroxy-24-oxo-5β-cholan-24-yl)amino]benzenesulfonic acid
$NH(m\text{-}(C_6H_4))SO_3H$
3-[(3α,7α,12α-trihydroxy-24-oxo-5β-cholan-24-yl)amino]benzenesulfonic acid
$NH(CH_2)_2SO_2H$
2-[(3α,7α,12α-trihydroxy-24-oxo-5β-cholan-24-yl)amino]ethanesulfinic acid
Glycocholate $NHCH_2CO_2H$
3α,7α,12α-Trihydroxy-5β-cholan-24-oic acid N-(carboxymethyl)amide
OR 1-[(3α,7α,12α-trihydroxy-24-oxo-5β-cholan-24-yl)amino]methanecarboxylic acid
$NH(CH_2)_2CO_2H$
2-[(3α,7α,12α-trihydroxy-24-oxo-5β-cholan-24-yl)amino]ethanecarboxylic acid
$NH(CH_2)_2CONH(CH_2)_2CO_2H$
6-[(3α,7α,12α-trihydroxy-24-oxo-5β-cholan-24-yl)amino]-(4-amido)hexanecarboxylic acid
$NH(CH_2)_3CO_2H$
3-[(3α,7α,12α-trihydroxy-24-oxo-5β-cholan-24-yl)amino]propanecarboxylic acid
$NH(CH_2)_3CONH(CH_2)_3CO_2H$
8-[(3α,7α,12α-trihydroxy-24-oxo-5β-cholan-24-yl)amino]-(5-amido)octanecarboxylic acid
$O(CH_2)_2SO_3H$
2-[(3α,7α,12α-trihydroxy-5β-cholan-24-oyl)oxy]ethanesulfonic acid

EXAMPLES

Materials and Methods

Materials—Taurocholate and amino acid analogs were purchased from Sigma-Aldrich Corporation (St. Louis, Mo.), Steraloids (Newport, R.I.) or were synthesized in the Abel-Santos laboratory. Reagents for synthesis were purchased from Sigma-Aldrich Corporation (St. Louis, Mo.) or Alpha Aesar (Ward Hill, Mass.). Thin layer chromatography silica gel 60 $F_{254}$ was purchased from EMD Chemicals (Gibbstown, N.J.). Silica gel for column chromatography was purchased from Fisher Scientific (Pittsburg, Pa.).

Synthesis of 3-methoxy-7,12-dihydroxytaurocholate (T09), 3,7-dimethoxy-12-hydroxytaurocholate (T10)-Methoxylated taurocholate analogs (T09 and T10) were prepared following published procedures (Bandyopadhyay, P., V. Janout, L.-Zhang, and S. L. Regen. 2001. Ion conductors derived from cholic acid and spermine: Importance of facial hydrophilicity on Na+ transport and membrane selectivity. J. Am. Chem. Soc. 123(31):7691-7696). Briefly, to a solution of taurocholate (1 equivalent) in dry 1,4-dioxane, methyl iodide (50 equivalents) and sodium hydride (4 equivalents) were added under nitrogen. The reaction was heated to 40° C. for 48 hours with stirring. After the initial 48 hours sodium hydride (4 equivalents) was added daily to the reaction for four additional days. The reaction was then diluted with dichloromethane, washed with 1M HCl, and twice with water. The organic layer was dried over anhydrous sodium sulfate and the solvent was removed under reduced pressure. The resulting residue was purified by silica gel column chromatography eluted with a step gradient from 100% dichloromethane to 60% dichloromethane/acetone. Two different compounds were obtained. $^1$H-NMR and mass spectrometry showed that one compound had a single methoxy group and the second compound had two methoxy groups. The compounds were tentatively identified as 3-methoxy-7,12-dihydroxytaurocholate (T09) and 3,7-dimethoxy-12-hydroxytaurocholate (T10) as determined by published OH reactivity (Gargiulo, D., T. A. Blizzard, and K. Nakanishi. 1989. Synthesis of mosesin-4, a naturally occurring steroid saponin with shark repellent activity, and its analog 7-β-galactosyl ethyl cholate. Tetrahedron. 45(17):5423-5432. Iida, T. and F. C. Chang. 1982. Potential bile acid metabolites. 6. Stereoisomeric 3,7-dihydroxy-5β-cholanic acids. J. Org. Chem. 47(15):2966-2972.).

Synthesis of CAAMSA (T11), CAAPSA (T12), CApSA (T13), CAoSA (T14), CAmSA (T15), hypotaurocholate (T16), CAAPA (T18), CA2APA (T19), CAABA (T20), and CA2ABA (T21)—Taurocholate analogs T11-T16 and T18-T21 were prepared following published procedures (Dayal, B., K. R. Rapole, C. Patel, B. N. Pramanik, S. Shefer, G. S. Tint, and G. Salen. 1995. Microwave-induced rapid synthesis of sarcosine conjugated bile acids. Bioorg. Med. Chem. Lett. 5(12):1301-1306. Tserng, K. Y., D. L. Hachey, and P. D. Klein. 1977. An improved procedure for the synthesis of glycine and taurine conjugates of bile acids. J. Lipid Res. 18(3):404-407.). Briefly, cholic acid (1 equivalent) was activated with 1.4 equivalents of N-ethoxycarbonyl-2-ethoxy-1, 2-dihydroquinoline (EEDQ) and 1.3 equivalents N-methylmorpholine (NMO) in dimethylformamide (DMF). After stirring for 5 minutes, 1.2 equivalents of the appropriate amino sulfonic acid or amino acid were added. The reaction was heated to 90° C. for 40 min and then cooled to room temperature. The solution was poured into 100 ml of ice-cold diethyl ether resulting in a precipitate. The ether suspension was kept at 4° C. overnight. The ether layer was decanted and the resinous residue was dissolved in 25 ml 0.2 N NaOH/MeOH and poured into 100 ml cold, diethyl ether. The ether solution was kept at 4° C. for at least 2 hours and the resulting precipitate was filtered and washed with diethyl ether. If necessary, the product was recrystallized by dissolving in hot ethanol to saturation followed by the addition of ethyl acetate until a precipitate appeared. The solution was kept at −20° C. for 2 hours to allow complete precipitation and then filtered to retrieve product. The precipitated residue was further purified by silica gel column chromatography eluted with a step gradient from 100% dichloromethane to 100% ethanol. CA2APA (T19) and CA2ABA (T21) were obtained as side products of the synthesis of CAAPA (T18), and CAABA (T20), respectively. Compound structures were verified by $^1$H-NMR, FT-IR, and mass spectrometry.

Synthesis of CAHESA (T22)—Conjugation of cholate to the sulfonic acid alkyl linker by an ester was prepared following established protocols for Fischer esterification (e.g., Fischer, E. and A. Speier. 1895. Darstellung der Ester. Ber. 28(3):3252-3258. Indu, B., W. R. Ernst, and L. T. Gelbaum.

1993. Methanol-formic acid esterification equilibrium in sulfuric acid solutions: Influence of sodium salts. Ind. Eng. Chem. Res. 32(5):981-985.). Briefly, to a solution of cholate (1 equivalent) and hydroxy ethane sulfonic acid (4 equivalents), concentrated sulfuric acid was added dropwise and refluxed for one hour. The reaction was poured into cold diethyl ether and a precipitate formed immediately. The diethyl ether suspension was left overnight at 4° C. The precipitate was filtered, dissolved in 0.2 N NaOH/MeOH, precipitated a second time in diethyl ether, and kept at 4° C. for at least 2 hours. The crude precipitate was filtered and purified by silica gel column chromatography eluted by step gradient from 100% dichloromethane to 30% dichloromethane/EtOH. The compound structure was verified by $^1$H-NMR, FT-IR, and mass spectrometry.

Bacterial Strains and Spore Preparation—*Clostridium difficile* strain 630 (ATCC BAA-1382) was obtained from the American Type Culture Collection (ATCC). *C. difficile* cells were plated in BHIS agar supplemented with 1% yeast extract, 0.1% L-cysteine HCl and 0.05% sodium taurocholate to yield single cell clones. Single *C. difficile* colonies were grown in BHIS broth and spread plated onto agar to obtain bacterial lawns. Plates were incubated for 5 days at 37° C. in an anaerobic environment (5% $CO_2$, 10% $H_2$, and 80% $N_2$). The resulting bacterial lawns were collected by flooding with ice-cold deionized water. Spores were pelleted by centrifugation and resuspended in fresh deionized water. After two washing steps, spores were separated from vegetative and partially sporulated forms by centrifugation through a 20%-50% HistoDenz gradient. The spore pellet was washed five times with water, resuspended in sodium thioglycollate (0.5 g/liter) and stored at 4° C.

Activation of *C. difficile* Spore Germination by Amino Acids and Taurocholate Analogs—Spores were diluted in germination buffer (100 mM sodium phosphate buffer (pH 6.0) containing 5 mg/ml sodium bicarbonate) to an $OD_{580}$ of 1.0. To test for taurocholate agonists of spore germination, spore suspensions were individually supplemented with 6 mM of the corresponding taurocholate analogs and 12 mM glycine. To test for amino acid agonists of spore germination, spore suspensions were supplemented with 12 mM of the corresponding amino acid analogs and 6 mM taurocholate. Spore germination was evaluated based on decrease in $OD_{580}$ at 30° C. each minute for 90 min. Germination rates were set to 100% for *C. difficile* spores germinated with 6 mM sodium taurocholate and 12 mM glycine. Percentage germination for all analogs was calculated as the fraction of germination rate compared to these conditions.

Inhibition of *C. difficile* Spore Germination by Amino Acids and Taurocholate Analogs—To test for antagonists of spore germination, spore aliquots were individually supplemented with varying concentration of taurocholate analogs or amino acid analogs. Spore suspensions were incubated for 15 min at room temperature while monitoring $OD_{580}$. If no germination was detected, taurocholate and glycine were added to 6 and 12 mM final concentrations, respectively. Relative $OD_{580}$ values were obtained every minute for 90 minutes after germinant addition and were plotted against the logarithm of inhibitor concentrations. As expected, germination decreased in the presence of active germination inhibitors. The resulting data were fitted using the four parameter logistic function SigmaPlot v.9 software to obtain $IC_{50}$ values (Rodbard, D. and Y. Feldman. 1978. Kinetics of two-site immunoradiometric ('sandwich') assays. I. Mathematical models for simulation, optimization, and curve fitting. Mol. Immunol. 15(2):71-76. Rodbard, D. and S. W. McClean. 1977. Automated computer analysis for enzyme multiplied immunological techniques. Clin. Chem. 23(1):112-115.).

*C. difficile* Spore Germination in BHIS Media—To test for germination in complex media, spores were resuspended in brain heart infusion broth supplemented with 5 mg/ml yeast extract and 0.1% L-cysteine (BHIS) alone and with combinations of taurocholate, chenodeoxycholate, glycocholate, glycine, L-arginine, and L-phenylalanine. Bile salts were added to a final concentration of 6 mM and amino acids were added at a final concentration of 12 mM. Relative $OD_{580}$ values were obtained every minute for 90 minutes after germinant addition.

*C. difficile* has been shown to germinate in the presence of glycine and taurocholate (35). The question that has remained unanswered is how glycine and taurocholate interact with the putative binding sites. In the current work, we have tested 30 amino acid analogs and 22 taurocholate analogs as activators (FIG. 1A) or inhibitors of *C. difficile* spore germination (FIG. 1B). Structure-activity relationship analysis of germinant analogs allows a better understanding of the microenvironment of the *C. difficile* germination machinery. Activators of the germination pathway identify which functional groups are essential for binding and activation of the *C. difficile* germination machinery. On the other hand, inhibiting agents provide structural details about functional groups that allow only binding. Inhibition assays serve as an indirect method to map physiochemical configurations in receptor binding sites. Competitive inhibitors most likely bind to the same site as the cognate germinant. Strong competitive inhibitors will complement the germinant binding site shape, size, hydrophobicity, and hydrogen bonding pattern. Inactive compounds yield information on functional groups that interfere with germinant binding. As expected, changing glycine and taurocholate functional groups affected the germination of *C. difficile* spores.

Glycine (A01) has a methylene bridge that separates the carboxylic and amine groups and is the simplest of the 20 common amino acids. To find determinants required for glycine recognition, we individually supplemented taurocholate-treated spores with 30 different glycine analogs (FIG. 2). Each of the glycine analogs differ from the parent compound by a single modification, either in the length of the alkyl chain, substitutions to the amino group, or changes in the carboxylate group. β-Alanine (A02) and γ-aminobutyric acid (A03) have an ethylene and a propylene bridge between the amino and carboxylate group, respectively. These changes progressively increase the distance between the amino and carboxylate groups. β-Alanine (A02) and γ-aminobutyric acid (A03) are as effective as glycine as co-germinants of *C. difficile* spores (FIG. 3). Thus, lengthening the chain between the amino and carboxylate functional groups does not interfere with recognition by the putative glycine germination receptor.

Aminomethylphosphonic acid (A04) is a glycine analog where the carboxylate has been changed to a phosphonate. This substitution exchanges a carbon atom for phosphorus while retaining the negative charge. Aminomethylphosphonic acid (A04) significantly decreased *C. difficile* spore germination (FIG. 3). Furthermore, methylation of the carboxylate in glycine methyl ester (A05) resulted in germination rates of less than 10% compared to glycine-triggered germination. Any other modification of the carboxylate (glycine ethyl ester (A06), glycinamide (A07), glycine hydroxamate (A08)) resulted in compounds that were unable to activate or inhibit *C. difficile* spore germination (data not shown). The sum of these data suggests that there is a specific requirement for a carboxylate functional group for recognition by the glycine germination receptor to activate germination.

The distance between the amino and carboxylate of diglycine (A09) is similar to γ-aminobutyric acid (A03). However, whereas γ-aminobutyric acid (A03) is a good agonist for *C. difficile* spore germination, diglycine (A09) has no effect (data not shown). Thus the addition of an internal amide must interfere with compound binding. Possibly there is a requirement for a more hydrophobic linker between the two functional group ends. Glycine anhydride (A10) is the result of the dehydration of diglycine, forming a cyclic diamide. Without a free amine or carboxylate, this compound is unable to activate or inhibit spore germination (data not shown). The rigidity and bulkiness of this analog may prevent interaction with the glycine binding site.

Alkylation (sarcosine (A11), N,N-dimethylglycine (A12), betaine (A13)), acetylation (N-acetylglycine (A14)), or other modification (nitrilotriacetic acid (A15)) to the amino group of glycine resulted in compounds that can neither activate nor inhibit *C. difficile* spore germination (data not shown). This suggests that activation of *C. difficile* spores by glycine has a requirement for a free primary amino group regardless of an unmodified carboxylate group. To test the effect of side-chain substitution in amino acid recognition by the *C. difficile* germination machinery, we exposed taurocholate-treated *C. difficile* spores to other amino acid analogs (FIG. 2). L-alanine (A16) has been shown to act as germinant and/or co-germinant in other sporulating bacteria (Abel-Santos, E. and T. Dodatko. 2007. Differential nucleoside recognition during *Bacillus cereus* 569 (ATCC 10876) spore germination. New J. Chem. 31(5):748-755.). The stereoisomer, D-alanine (A17), has been shown to inhibit alanine-mediated germination in *Bacillus* (Preston, R. A. and H. A. Douthit. 1988. Functional relationships between L- and D-alanine, inosine and NH4Cl during germination of spores of *Bacillus cereus*. T. J. Gen. Microbiol. 134(11):3001-3010.). In *C. difficile*, L-alanine (A16) was as efficient at triggering germination as glycine (A01) (FIG. 3). Interestingly, D-alanine (A17) was unable to inhibit germination of spores treated with L-alanine and taurocholate (data not shown). D-alanine was also inactive as an agonist for *C. difficile* spore germination (data not shown). This implies that stereochemistry is important for recognition and binding of amino acids.

To determine whether amino acid analogs with longer, linear alkyl side chains were able to activate *C. difficile* spore germination, we exposed taurocholate-treated spores to L-2-aminobutyric acid (A18) and L-norvaline (A19). Both of these amino acid analogs were able to activate germination to levels similar to glycine (A01). L-valine (A20) is a branched isomer of L-norvaline (A19) and has similar chemical and physical properties. However, this slight difference in structure reduced *C. difficile* spore germination by more than 90% compared to L-norvaline (FIG. 3). Similarly, L-isoleucine (A21) and L-leucine (A22) are poor germinants of *C. difficile* spores compared to L-norvaline (A19). The data suggests that branched alkyl side chains are unable to be recognized by the putative amino acid germination receptor in *C. difficile.*

L-cysteine (A23) is an amino acid with a methanethiol side chain. L-serine (A24), on the other hand, is an L-cysteine analog where the thiol group is substituted for a hydroxyl group. Interestingly, whereas L-cysteine (A23) is a good germinant of *C. difficile* spores (FIG. 3), the more polar L-serine (A24) is almost inactive. The germination activity of L-cysteine (A23) is not due solely to hydrophobicity since the more hydrophobic L-methionine (A25) is a poor germinant compared to L-cysteine (A23). This suggests that *C. difficile* spores recognize the thiol group specifically as a determinant for germination.

Surprisingly, L-phenylalanine (A26), with a bulky aromatic side chain, is as effective as glycine as a germinant of *C. difficile* spores (FIG. 3). We would expect that since branched amino acids are inactive, the bulkier side chain of L-phenylalanine would also be restricted from the binding site. We cannot completely rule out that the putative glycine receptor is able to accommodate phenyl, but not branched alkyl side chains. However, we find that possibility unlikely due to their relative size compared to glycine. Hence, we postulate that aromatic amino acids are recognized by a separate binding site in the *C. difficile* spore. Indeed, other *Bacillus* and *Clostridium* are able to recognize structurally different germinants by encoding multiple receptors (e.g., Dodatko, T., M. Akoachere, N. Jimenez, Z. Alvarez, and E. Abel-Santos. 2010.

Dissecting interactions between nucleosides and germination receptors in *Bacillus cereus* 569 spores. Microbiology. 156(4):1244-1255. Foster, S. J. and K. Johnstone. 1990. Pulling the trigger: The mechanism of bacterial spore germination. Mol. Microbiol. 4(1):137-141.).

L-arginine (A27) is also a strong co-germinant for *C. difficile* spores (FIG. 3). Although L-arginine has a linear alkyl chain, it also contains a positively charged, branched guanidinium group. Similarly, L-lysine (A28) is linear with a positively charged amino side chain. Yet L-lysine (A28) is a weak germinant compared to L-arginine. L-histidine (A29) contains an aromatic side chain like L-phenylalanine (A26) but is positively charged like L-arginine's (A27) side chain. However, unlike L-phenylalanine (A26) or L-arginine (A27), L-histidine (A29) could not efficiently activate *C. difficile* spore germination. L-aspartic acid (A30) has a short acidic side chain and was similarly unable to affect *C. difficile* spore germination (data not shown). Thus, L-arginine (A27) was the only polar and/or charged amino acid tested that was able to induce *C. difficile* spore germination. Since L-arginine (A27) has physicochemical properties that are very different from the other amino acids able to activate *C. difficile* spore germination, it suggests there is a specific recognition site for L-arginine binding.

Earlier studies (Sorg, J. A. and A. L. Sonenshein. 2008. Bile salts and glycine as cogerminants for *Clostridium difficile* spores. J. Bacteriol. 190(7):2505-2512.) reported that only glycine was able to trigger *C. difficile* spore germination in the presence of taurocholate. This study reportedly used three combinations of defined media to narrow down active germination stimulators. Although glycine was supplemented with only seven amino acids, phenylalanine and arginine were in mixture supplemented with 15 other amino acids. The presence of multiple weak germinants in the defined media containing phenylalanine and arginine could mask their ability to stimulate germination. Furthermore, in those experiments L-phenylalanine and L-arginine were supplemented at lower concentrations (1.21 mM and 1.15 mM, respectively) than used for the current experiments (12 mM).

Glycine, L-arginine, and L-phenylalanine individually or in pairs do not trigger *C. difficile* spore germination in the absence of taurocholate (data not shown). However, a cocktail of L-phenylalanine, L-arginine, and glycine (all at 12 mM) was able to effectively trigger *C. difficile* spore germination in the absence of taurocholate (FIG. 4). Chenodeoxycholate (6 mM) is not able to inhibit spore germination of *C. difficile* spores treated with amino acids only. Other Clostridia have been shown to use amino acids alone as germination signals (Ramirez, N. and E. Abel-Santos. 2010. Requirements for germination of *Clostridium sordellii* spores in vitro. J. Bacteriol. 192(2):418-425.).

When *C. difficile* spores are resuspended in BHIS media, germination is very slow even though BHIS contains a complex amino acid mixture that includes glycine, L-arginine, and L-phenylalanine (FIG. 4). It is possible that BHIS contains amino acids that are weak germinants and will compete with glycine, L-phenylalanine, and L-arginine for binding. Binding of these alternative substrates will cause a fraction of the spore population to germinate at a slower rate. We have seen similar behavior in the germination of *C. sordellii* spores (27). Interestingly, supplementing BHIS with taurocholate (FIG. 5, T01) augmented *C. difficile* spore germination (FIG. 4). The taurocholate-enhanced spore germination in BHIS was inhibited by chenodeoxycholate. Thus, it seems that amino acid-only *C. difficile* spore germination occurs only when a limited number of amino acids are present and is disfavored with complex amino acid mixtures.

All glycine analogs and amino acids were further tested for their ability to inhibit *C. difficile* spore germination. Spores were treated with each analog or amino acid in the presence of taurocholate and glycine. However, no individual amino acid analog inhibited *C. difficile* spore germination (data not shown).

Taurocholate (T01) is a natural bile salt that has hydroxyl groups at position 3, 7, and 12 of the cholate skeleton. All three hydroxyl groups are in the alpha-configuration. Taurocholate also has a side chain consisting of taurine attached to the cholate skeleton by an amide bond. Taurocholate activates *C. difficile* spore germination with an $EC_{50}$ of 15.9 mM. Taurocholate analogs were tested for their ability to activate germination in the presence of glycine and for their ability to inhibit germination in the presence of taurocholate and glycine.

To understand the importance of hydroxyl groups on the cholate backbone of taurocholate, analogs T02-T08 (FIG. 5) were tested as agonists and antagonists of *C. difficile* spore germination. These analogs differ from taurocholate (T01) in the number, placement, or stereochemistry of the hydroxyl groups. Taurodeoxycholate (T02) lacks only the hydroxyl group at the 7-position. This change was sufficient to reduce germination by more than 70% (Table 1). Meanwhile, taurochenodeoxycholate (T03) is only missing the hydroxyl at position 12 and was only able to induce germination to 10% of taurocholate. Tauroursodeoxycholate (T04) is an isomer of taurochenodeoxycholate (T03) where the 7-hydroxyl is in the beta-configuration. The alteration of stereochemistry of this one hydroxyl group further decreased germination activity from 10% for taurochenodeoxycholate (T03) to 3% for tauroursodeoxycholate (T04) (Table 1).

As expected, taurolithocholate (T05) and taurocholanate (T06) that lack hydroxyls at positions 7, 12 and 3, 7, 12, respectively are unable to activate germination. Taurohycholate (T07) and taurohyodeoxycholate (T08) are isomers of taurocholate (T01) and taurodeoxycholate (T02), respectively where the 12-hydroxyl groups were moved to the 6-position. Neither of these compounds is able to significantly activate germination of *C. difficile* spores. The sum of these data suggests that both the 7 and 12 α-hydroxyls of taurocholate are important determinants for binding and activation of *C. difficile* spores.

The 3-hydroxyl position of the cholate molecule is more nucleophilic than the other two hydroxyls. Similarly, the 7-hydroxyl is more reactive than the 12-hydroxyl (13, 15). Thus, methylation of taurocholate yielded two compounds that we putatively identified as 3-methoxy-7,12-dihydroxytaurocholate (T09) and 3,7-dimethoxy-12-hydroxytaurocholate (T10). Interestingly, 3-methoxy-7,12-dihydroxytaurocholate (T09) neither induces nor inhibits *C. difficile* spore germination. As expected, 3,7-dimethoxy-12-hydroxytaurocholate (T10) was also inactive. This suggests that the 3-hydroxyl hydrogen bond donating ability is essential for recognition of taurocholate as a germinant *C. difficile* spores.

To determine if analogs differing in the number, location, or stereochemistry of the hydroxyl groups can inhibit taurocholate mediated germination, *C. difficile* spores were treated with taurocholate (T01), glycine (A01), and compounds T02-T10 (Table 1). Only taurochenodeoxycholate (T03), tauroursodeoxycholate (T04) and taurohyodeoxycholate (T08) showed germination inhibitory properties. All three inhibitors have the common feature of lacking the 12-hydroxyl group. Since the 12-hydroxyl group was necessary for triggering spore germination, these results suggest that this hydroxyl is necessary for activation of germination but not for binding of taurocholate to the putative *C. difficile* germination receptor. The inhibitory compounds also have hydroxyl groups at either the 6- or 7-positions (but not both) indicating that having one (but not two) hydroxyl in the B-ring is important for inhibition of taurocholate-mediated germination of *C. difficile* spores.

To determine taurine side chain functional groups responsible for recognition by the *C. difficile* germination machinery, analogs T11-T22 were tested for the ability to induce spore germination in the presence of glycine (FIG. 5). All these compounds differ from taurocholate in the structure of the side chain and retain the cholate skeleton with hydroxyl groups at the 3, 7, and 12 positions.

CAAMSA (T11) is a taurocholate analog where the alkyl linker between the sulfonate and the amide was shortened by one methylene. CAAPSA (T12), on the other hand is a taurocholate analog where the linker was lengthened by one methylene (FIG. 5). The results show that spores treated with CAAMSA (T11) germinate to levels comparable with spores treated with taurocholate (T01) (Table 2). In contrast the longer alkyl chain, CAAPSA (T12), does not activate germination. To further analyze the necessity of the alkyl linker on germination, we synthesized three analogs containing a benzene ring in place of the ethylene linker of taurine (FIG. 5). These analogs differed in the position of the sulfonate, para (CApSA, T13), ortho (CAoSA, T14), or meta (CAmSA, T15), with respect to the amino group in the benzene ring. These three taurocholate analogs were unable to activate *C. difficile* spore germination. This suggests that *C. difficile* spores are activated by taurocholate analogs with shorter, but not longer or bulkier linkers.

Hypotaurocholate (T16) differs from taurocholate by a substitution of the sulfonate for a sulfinate (FIG. 5). This analog was unable to activate *C. difficile* spore germination. Interestingly, glycocholate (T17) is a CAAMSA (T11) analog where the sulfonate has been substituted for a carboxylate. In our hands, glycocholate (T17), like CAAMSA (T11) is able to significantly activate *C. difficile* spore germination in buffer (Table 2). A previous report had determined that glycocholate (T17) is not a germinant for *C. difficile* spores in BHIS media (35). Indeed, when we tested glycocholate (T17) in BHIS media, *C. difficile* spore germination rate dropped almost 10-fold. However, addition of glycine to BHIS media partially restored glycocholate-mediated germination (data not shown). Hence, compound mixtures in BHIS media seem intrinsically inhibit *C. difficile* spore germination.

CAAPA (T18) is a carboxylated analog of taurocholate (T01). Interestingly, whereas taurocholate (T01), CAAMSA (T11) and glycocholate (T17) are able to activate *C. difficile* spore germination, CAAPA (T18) is inactive. Similarly, CA2APA (T19), CAABA (T20), and CA2ABA (T21) with longer side chains are also inactive. These results suggest that although a carboxylate is able to partially substitute for sulfonate, it is not optimal for activation of *C. difficile* spore germination.

CAHESA (T22) is a taurocholate analog where the amide group is substituted for an ester. CAHESA (T22) was unable to trigger germination in *C. difficile* spores (Table 2). This suggests that the hydrogen bond ability of the amide group is necessary for *C. difficile* spore germination.

To determine whether taurocholate analogs with modified side chains (T11-T22) (FIG. 5) can inhibit *C. difficile* spore germination, we analyzed the effect of these analogs on *C. difficile* spores treated with taurocholate (T01) and glycine (A01). Taurocholate analogs with one less carbon (T11) or one more carbon (T12) in the taurine side chain were unable to inhibit germination (Table 2). Interestingly, while the addition of a benzene ring in the linker with the sulfonate in the para (CApSA, T13) or the ortho (CAoSA, T14) position does not inhibit spore germination, having the sulfonate in the meta position (CAmSA, T15) results in strong inhibition of *C. difficile* spore germination. CAmSA (T15) has an $IC_{50}$ of 58.3 µM and is the strongest inhibitor reported so far. The conversion of the sulfonate functional group to a sulfinate (T16) resulted in a compound with slight inhibitory activity with an $IC_{50}$ of 640 µM. Interestingly, compounds with longer alkyl linkers followed by a carboxylate (T20-T21) are able to inhibit *C. difficile* spore germination whereas shorter carboxylate end groups (T17-T19) are inactive. CAABA (T20) has an $IC_{50}$ of 762 µM whereas the longer side chain, CA2ABA (T21), containing two amide groups has an $IC_{50}$ of approximately 3,000 µM. Replacement of the amide group of taurocholate for an ester (T22) results in a compound with slight inhibitory activity, $IC_{50}$ of 1,322 µM.

FIG. 1. Germination Kinetic Graphs Showing Agonistic and Antagonistic Behavior of Molecules with *C. difficile* Spores. (A) Activation of germination: *C. difficile* spores were treated with a fixed concentration of taurocholate (6 mM) and glycine was added at 0 mM (○), 8 mM (•), 10 mM (□), 12 mM (■), and 14 mM (Δ) final concentrations. For clarity, data is shown at five minutes intervals and only for five glycine concentrations. (B) Inhibition of germination: *C. difficile* spores were incubated with 0 mM (○), 0.0005 mM (•), 0.001 mM (□), 0.075 mM (■) and 7.5 mM (Δ) concentrations of CAmSA (T15) and supplemented with taurocholate (6 mM) and glycine (12 mM). For clarity, data is shown at five minutes intervals and only for five CAmSA (T15) concentrations. Although data was collected for 90 minutes, only 75 minutes are shown in both graphs for clarity.

FIG. 2. Amino Acids Assessed for Activation or Inhibition of Glycine-Mediated Germination in *C. difficile* Spores. Glycine (A01), β-alanine (A02), γ-aminobutyric acid (A03), aminomethylphosphonic acid (A04), glycine methyl ester (A05), glycine ethyl ester (A06), glycinamide (A07), glycine hydroxamate (A08), diglycine (A09), glycine anhydride (A10), sarcosine (A11), N,N-dimethylglycine (A12), betaine (A13), N-acetylglycine (A14), nitrilotriacetic acid (A15), L-alanine (A16), D-alanine (A17), L-2-aminobutyric acid (A18), L-norvaline (A19), L-valine (A20), L-isoleucine (A21), L-leucine (A22), L-cysteine (A23), L-serine (A24), L-methionine (A25), L-phenylalanine (A26), L-arginine (A27), L-lysine (A28), L-histidine (A29), L-aspartic acid (A30).

FIG. 3. Comparison of Amino Acids as Agonists of *C. difficile* Spore Germination. Spores were treated with taurocholate (6 mM) and amino acid analog at 12 mM. Germination was determined by the decrease in $OD_{580}$ for 90 minutes at 30° C. Percent germination for each analog was calculated based on glycine/taurocholate germination as 100%.

FIG. 4. Germination Kinetic Graph Showing Behavior of *C. difficile* Spores and Germinants in Buffer and Complex Media. *C. difficile* spores were resuspended in germination buffer and treated with L-phenylalanine, L-arginine, and glycine (each at 12 mM) (○), or L-phenylalanine, L-arginine, glycine (each at 12 mM) and chenodeoxycholate (6 mM) (•). Purified spores were also suspended in BHIS medium (□), BHIS supplemented with 12 mM taurocholate (▲), or BHIS supplemented with 12 mM taurocholate and 12 mM chenodeoxycholate (Δ). For clarity, data is shown at five minutes intervals and only for 75 minutes.

FIG. 5. Taurocholate Analogs Assessed for Activation or Inhibition of Taurocholate-Mediated Germination in *C. difficile* Spores. Taurocholate (T01), taurodeoxycholate (T02), taurochenodeoxycholate (T03), tauroursodeoxycholate (T04), taurolithocholate (T05), taurocholanate (T06), taurohycholate (T07), taurohyodeoxycholate (T08), 3-methoxy-7,12-dihydroxytaurocholate (T09), 3,7-dimethoxy-12-hydroxytaurocholate (T10), CAAMSA (T11), CAAPSA (T12), CApSA (T13), CAoSA (T14), CAmSA (T15), hypotaurocholate (T16), glycocholate (T17), CAAPA (T18), CA2APA (T19), CAABA (T20), CA2ABA (T21), CAHESA (T22)

In these examples, we used taurocholate and glycine analogs to better understand how the *C. difficile* germination machinery recognizes its germinants. Chemical probes can reveal chemical, physical, and spatial requirements of the germination receptor binding site. This present study has shown that *C. difficile* germination machinery recognizes a number of amino acid side chains and that the putative glycine receptor requires both a free carboxylate and a free amino group to recognize glycine, but the binding site is flexible enough to accommodate longer separations between the two functional groups. Alkyl amino acid side chains seem to be recognized in a narrow hydrophobic groove that allows the binding of linear chains but excludes branched isomers. We have seen a similar branched chain restriction in the recognition of inosine analogs by *B. cereus* spores (9). These size and polarity restrictions also suggest the existence of separate binding sites for L-phenylalanine, L-arginine and possibly L-cysteine.

We suggest that the binding region for L-alanine in *C. difficile* is divergent enough from the L-alanine binding site in *Bacillus* to impede the binding and inhibition by D-alanine. Because none of the amino acid analogs was able to compete with glycine to inhibit *C. difficile* spore germination, the functional groups in the amino acid moieties are needed for both binding and activation of the putative amino acid germination receptor.

The putative taurocholate binding sites of *C. difficile* spores were less flexible in compounds allowed to bind and activate germination. Hydroxyl groups at position 3 and 12 seem to be required for both binding and activation of *C. difficile* spore germination. In contrast, hydroxyl groups in the B-ring appear to be important only for binding. Hence, the data implies there is a requirement for hydrogen bonding with hydroxyls at specific locations and configurations in the *C. difficile* germination binding pocket.

Recognition of the taurine side chain seems to be even more restricted. Even small changes in linker length and rigidity, amide bond, or oxidation state of the sulfonate group had a large effect on *C. difficile* spore germination. Although the sulfonate group is optimal for spore germination activation, it can be partially substituted with a carboxylate as long as the alkyl chain is short. This data suggests that the binding site for taurocholate recognizes the taurine side chain selectively.

In contrast to agonist specificity, the putative taurocholate binding receptor was more flexible in regards to antagonist binding. The meta-sulfonic benzene derivative CAmSA (T15), is active at concentrations approximately 275-fold lower than taurocholate and is almost 4 times more active than the natural inhibitor chenodeoxycholate. The benzene ring is a rigid functional group with little free rotation. We speculate the sulfonate in the meta position is able to fit tightly into the sulfonate binding pocket but the overall receptor does not recognize the benzene ring to trigger germination. This is further confirmed by the inactivity of the ortho and para isomers that would spatially place the sulfonate in different locations. The rigidity and positioning of the m-sulfonate probably provides an entropic advantage over alkyl sulfonates. It is possible that longer alkyl side chains are too flexible to allow the sulfonate moiety to bind efficiently to the putative taurocholate. The discovery of CAmSA (T15) and its strong inhibitory effect has revealed a new path to designing compounds for CDI prophylaxis.

Interestingly, BHIS media seem to have intrinsic inhibitory activity against amino acid (but not taurocholate) activation of *C. difficile* spore germination. Since biological media is a better representation of potential metabolites present in the host, it indicates that taurocholate-mediated germination is the prefer pathway for human infection.

In conclusion, the putative taurocholate glycine receptors in *C. difficile* recognize multiple functional groups in their respective germinants. Hence, even subtle changes in the germinant structure can be detrimental to the binding ability of the germination machinery of *C. difficile* spores.

Recent Findings Regarding the Prophylactic Activity of CamSA on *Clostridium difficile* Infection i. Testing for CamSA toxicity in mice: Before we embarked in establishing a CDI animal model, we tested for CamSA toxicity in mice following a modification of the Fixed Dose Procedure (FDP). To determine acute toxicity of CamSA, groups of 5 animals were treated for 3 consecutive days with single gavage doses of 50 mg/Kg CamSA in DMSO. Animals were observed for 5 days for signs of toxicity (e.g. weight loss, diarrhea, hunch back, lethargy). Treated animals showed no signs of toxicity and were indistinguishable from animals treated with neat DMSO or neat water. Since no toxicity was observed, a second group of animals was dosed at 300 mg/Kg CamSA. As above, no signs of toxicity were apparent at this higher dose.

ii. Preparation of *C. difficile* spores for CDI challenge: A literature review showed that different conditions for *C. difficile* sporulation have been used to prepare spores for murine CDI challenge. More importantly, the published work establishing a mouse CDI model did not report spore purity. Furthermore, vegetative *C. difficile* cells were used to create a mouse relapse model for CDI, but no spore quantification was reported either. In our experience, growth conditions can affect the extent of sporulation and impure spore preparations can affect germination kinetics (1). Because of these issues, our laboratory has established details protocols to purify *C. difficile* spores to homogeneity.

To determine the effect of spore purity on CDI establishment, we prepared *C. difficile* spores using methods reported in two mice CDI models. We also tested *C. difficile* spore preparations that were purified following procedures from our laboratory. Furthermore, we tested two different *C. difficile* strains. *C. difficile* strain VPI 10463 has been used to induce mouse CDI, but sporulates poorly. *C. difficile* strain 630 produces abundant spores, but has not been tested in the CDI mouse model. The amount of spores produced under each condition was measured by microscopy observation of Schaeffer-Fulton stained aliquots. As expected, strain VPI 10463 yielded low amounts of spores, while strain 630 yielded large quantities of spores. Using sporulation conditions reported for the mouse CDI model, yielded preparation that consisted almost exclusively of vegetative cells (<5% spores).

iii. Refining the mouse CDI model: Each spore preparation above was used to infect groups of 5 mice with $10^6$ CFU of spores following published procedures. Under these conditions, purified spores from both the VPI 10463 and 630 strains caused CDI symptoms in mice (diarrhea, weight loss, wet-tail, lethargy). In contrast, mice challenged with *C. difficile* vegetative cells did not develop CDI. Similar results were observed when mice the initial dose of *C. difficile* spores or vegetative cells were increased to $10^8$ CFU. From these experiments we established that the best conditions to establish CDI involves highly purified *C. difficile* strain 630 spores.

iv. Testing CamSA as CDI prophylaxis: To determine if CamSA protects mice from CDI, groups of five mice were treated with 5, 25, 50 or 300 mg/kg of either CamSA (a germination inhibitor) or taurocholate (a germination activator) in DMSO. A third group was given neat DMSO. Each group was then infected with $10^8$ CFU of purified *C. difficile* strain 630 spores. Each group was given repeated doses of CamSA, taurocholate or DMSO at 24 and 48 hours post-challenge. All animals were weighted twice a day and monitored for CDI symptoms. As above, DMSO-treated animals developed CDI in the first 48 hours after challenge. Similarly, all taurocholate-treated animals developed CDI. In contrast, animals treated with 50 or 300 mg/Kg CamSA did not develop CDI and were undistinguishable from non-infected animals. Animals treated with 5 or 25 mg/Kg CamSA developed CDI, but disease onset and severity were less pronounced than either DMSO or taurocholate treated animals. Thus, CamSA, but not taurocholate, is able to prevent CDI in mice (Table 1).

v. Testing CamSA dosage timing in CDI prevention: To determine the latest time point for effective CamSA prophylaxis, antibiotic treated mice were infected with $10^8$ CFU of purified *C. difficile* strain 630 spores. Mice were divided into four groups. Groups I, II, III, and IV were given a 300 mg/Kg dose of CamSA at 0, 3, 6, and 12 hours after spore challenge, respectively (Table 2). A second dose of CamSA was administered 24 hours after the first dose. All animals were weighted twice a day and monitored for CDI symptoms. Animals treated with CamSA at 0, 3, and 6 hours post-infection did not develop any CDI symptoms and were undistinguishable from control animals. In contrast, all animals treated with CamSA at 12 hours post-infection developed CDI symptoms. Although the onset of the disease was delayed by 24 hours compared to DMSO-treated animals, the severity of the disease was not abated. This data shows that there is at least a 6 hour window for CamSA to be effective in CDI prevention. Even more, spore germination is a required first step that occurs prior to the appearance of CDI symptoms. Thus, the protective effect of CamSA can be used to estimate that *C. difficile* spore germination occurs between six hours and 12 hours after *C. difficile* spore ingestion.

TABLE 1

Testing CamSA as CDI prophylactic

| Treatment | Animals with CDI symptoms | Average weight change 3 days post challenge |
|---|---|---|
| DMSO | 4/4 | −12% |
| Taurocholate | 3/3 | −18% |
| CamSA (300 mg/Kg) | 0/5 | +06% |
| CamSA (50 mg/Kg) | 0/5 | +05% |
| CamSA (25 mg/Kg) | 5/5 | −05% |
| CamSA (5 mg/Kg) | 5/5 | −8% |

TABLE 2

Testing CamSA dosage timing

| Group | First CamSA dose after challenge (h) | Animals with CDI symptoms |
|---|---|---|
| I | 0 | 0/5 |
| II | 3 | 0/5 |
| III | 6 | 0/5 |
| IV | 12 | 5/5 |

In FIG. 7,

[a]*C. difficile* spores were individually treated with 6 mM glycine and 12 mM taurocholate analogs T11-T22. Percent germination was calculated based on taurocholate/glycine germination as 100%. Standard deviations are shown in parentheses.

[b]*C. difficile* spores were incubated with various concentrations of taurocholate analogs for 15 minutes prior to addition of 6 mM taurocholate and 12 mM glycine. $IC_{50}$ was calculated by plotting extent of germination vs. the logarithm of analog T11-T22 concentration. Standard deviations are shown in parentheses. N/A, No activity under the conditions tested.

FIG. 10 is a graph of results from mice treated with CamSA or chenodeoxycholate. The graph shows no weight changes. Groups of five mice were treated with DMSO (□), 50 mg/kg chenodeoxycholate (◇), 50 mg/kg CamSA (Δ), or 300 mg/kg CamSA (○). Animal weight was obtained daily.

FIG. 11 displays graphic results of protection of mice from CDI by different bile salts. The data is shown in a Kaplan-Meier survival plot for *C. difficile* infected mice treated with DMSO (◇), 300 mg/kg taurocholate (Δ), 50 mg/kg chenodeoxycholate (○), 50 mg/kg CamSA (♦), or 300 mg/kg ethylcholate (X). Non-infected animals were used as control (□).

FIG. 12 shown graphic representations of signs of severity for *C. difficile* infected animals treated with different bile salts. Non-infected animals were used as control (panel A). Animals challenged with *C. difficile* spores were treated with three doses of DMSO (panel B), taurocholate (panel C), chenodeoxycholate (panel D), CamSA (panel E), or ethylcholate (panel F). The severity of CDI signs was scored using the Rubicon scale discussed above.

FIG. 13 is a graph that shows that CamSA does not affect vegetative bacterial growth. *E. coli* DH5α (□), *B. longum* (○), *L. gasseri* (Δ), and *C. difficile* (◇) were incubated in media supplemented with 0 or 10 mM CamSA. The $OD_{580}$ was recorded at 0, 1, 2, 3, 4, 6, and 8 hours. Growth inhibition was determined by subtracting optical density of CamSA-treated cultures from untreated control cultures.

FIG. 14 graphically shows that CamSA is not toxic to mammalian cells. Murine macrophages J774A.1 were treated with DMSO (panel A), 10% ethanol (panel B), or 200 µM CamSA (panel C). Cell viability was determined by trypan blue dye exclusion staining.

FIG. 15 graphically shows distribution of *C. difficile* spores in the GI tract of CamSA-treated animals. The stomach (St), duodenum (Du), jejunum (Je), and ileum (Il) showed negligible amounts of spores compared to the cecum (Ce) and colon (Co).

FIG. 16 is graphic evidence that CamSA protects mice from CDI. Comparison of CDI sign severity after 48 hours (white bars) and 72 hours (black bars) of animals challenged with *C. difficile* spores and treated with DMSO, 300 mg/kg taurocholate (TC), 50 mg/kg chenodeoxycholate (CDCA), 50 mg/kg CamSA, or 300 mg/kg ethyl cholate (EC). Non-challenged (NC) animals were used as controls. Clinical endpoint was set as >6 in the CDI sign severity scale (dashed line). None of the animals in the DMSO and EC groups survived to 72 hours post-challenged. Standard deviations represent at least five independent measures.

TABLE 3

| Compound | A→B[b] ($10^{-6}$ cm s⁻) | B→A[c] ($10^{-6}$ cm s⁻) | Efflux Ratio[d] | Comment[e] |
|---|---|---|---|---|
| Ranitidine | 0.3 | 1.8 | 5.3 | Low permeability control |
| Warfarin | 42.9 | 16.0 | 0.4 | High permeability control |
| CamSA | 0.0 | 10.9 | >2 | Low Permeability. substrate |

[a]All tests were performed at 10 µM final concentrations and equilibrated for two hours
[b]Apical to basolateral apparent permeability ($P_{app}$)
[c]Basolateral to apical apparent permeability ($P_{app}$)
[d]Efflux ratio (RE) >2 indicates a significant efflux activity, an indication of potential substrate for PGP or other active transporters
[e]Permeability ranking: Low ($P_{app}$ < 0.5), Moderate (0.5 < $P_{app}$ < 5), High ($P_{app}$ > 5)

FIG. 17 is a time line model for CDI onset in mice. *C. difficile* spores (black circles) that are ingested by the host. Spores rapidly transit through the upper GI tract and colonize the colon and cecum. Spore shedding begins less than 2 hours post-ingestion. Between 6 and 9 hours after ingestion sufficient numbers of spores germinate to establish infection. The outgrowing *C. difficile* cells (white circles) proliferate in the lower intestine, are shed, and can re-sporulate. A small amount of ingested spores remain in the lower intestine for more than 96 hours post ingestion.

CamSA had no observable adverse effects on mice. To determine the acute toxicity of CamSA to mice, we used the fixed dose procedure. No physical adverse effects or weight loss were observed when CamSA was administered for three consecutive days at doses up to saturating 300 mg/kg. A 300 mg/kg dose of chenodeoxycholate caused immediate death, probably due to observed precipitation of chenodeoxycholate upon interaction with mouse saliva and gastric juice. Chenodeoxycholate at 50 mg/kg did not cause any observable side effects.

Prevention of CDI by bile salt analogs. As previously reported, when mice were challenged with $10^8$ CFU of *C. difficile* spores, severe CDI signs developed and all animals reached clinical endpoint by 48 hours post-challenge. The large ($10^8$ CFUs) inoculum of spores ensured synchronized CDI onset and fast CDI sign progression. Mice treated with up to 300 mg/kg taurocholate or ethyl cholate also developed severe CDI and signs were undistinguishable from untreated animals. Mice treated with 50 mg/kg chenodeoxycholate developed moderate to severe signs of CDI, but onset was delayed by 24 hours. In contrast, all animals treated with 50 or 300 mg/kg CamSA showed no sign of CDI and were undistinguishable from uninfected animals. All asymptomatic animals remained free of CDI signs for at least 14 days post-challenge.

Stability of CamSA. CamSA is a taurocholate analog with an amide bond linking cholic acid to meta-aminobenzene sulfonic acid. To be effective, CamSA must survive the changing environments of the GI tract. To test for stability, CamSA was incubated in artificial gastric juice and intestinal juice. No degradation of CamSA was evident even after 24 hours incubation under both conditions (data not shown).

Bacterial bile salt hydrolases (BSHs) deconjugate primary and secondary bile salts. *B. longum* and *L. gasseri* are two intestinal bacteria commonly used as test strains for BSH production. After incubation with a culture of *B. longum* for 24 hours, CamSA and taurocholate are both hydrolyzed to cholic acid at similar rates. CamSA and taurocholate are less sensitive to degradation by BSHs secreted by *L. gasseri*. Less than 30% of either CamSA or taurocholate was hydrolyzed to cholic acid after 24 hours. *E. coli* does not produce BSH and both CamSA and taurocholate were stable after 24 hour incubation with *E. coli* cultures (data not shown). CamSA was not degraded in growth medium alone.

CamSA Caco-2 permeability. To prevent *C. difficile* spores from germinating, CamSA needs to be retained in the intestinal lumen. Caco-2 monolayers serves as an in vitro surrogate assay for intestinal permeability, absorption, and metabolism. CamSA was studied in a Caco-2 permeability assay and displayed an apical to basolateral apparent permeability coefficient ($P_{app}$) of $<10^{-6}$ cm/s and basolateral to apical $P_{app}$ of $10.9 \times 10^{-6}$ cm/s. The efflux ratio suggests that CamSA is a substrate for active transport. In both assays, CamSA was recovered at 100% indicating low binding, accumulation, and metabolism by Caco-2 cells.

Effect of CamSA on bacterial growth. *E. coli*, *B. longum*, and *L. gasseri* are indigenous mammalian gut bacteria and are continuously exposed to bile salts. As expected, growth of these bacteria was unaffected by the presence of CamSA in the growth medium. *C. difficile* cells also grew normally in the presence of CamSA.

Cytotoxicity of CamSA. Cell viability was qualitatively determined by visual observation of rounded/detached cells and trypan blue staining. CamSA-treated Vero, Caco-2, and macrophage cells appeared healthy and were undistinguishable from DMSO-treated cells. Cell viability was also quantitatively determined by ATP production. Vero and Caco-2 cells treated with 50 or 200 µM CamSA produced ATP at similar levels to healthy control cells.

CamSA protection of Vero and Caco-2 Cells: Spent media from outgrowing *C. difficile* spores killed Vero cells in a dose-dependent manner. These data are consistent with previous reports indicating that vegetative *C. difficile* secretes cell-killing toxins during growth. When *C. difficile* spores were incubated in medium containing 200 µM CamSA, bacterial growth was reduced but not eliminated. As expected, spent media from CamSA treated cultures were less effective at killing epithelial cells. Similar results were observed for Caco-2 cell cultures (data not shown).

Timing of CDI onset. To determine the onset of CDI in mice, animals were challenged with *C. difficile* spores and treated with 300 mg/kg CamSA between 0 and 12 hours post-challenge. All animals treated with CamSA up to 6 hours post-challenge were fully protected from CDI. In contrast, all animals treated with CamSA at 9 or 12 hours post-challenge developed severe CDI undistinguishable from untreated mice and reached the clinical endpoint 48 hours post infection (FIGS. 5A and 5B).

Similar to previous reports, GI contents from animals with CDI signs contained almost exclusively *C. difficile* vegetative cells. These animals started to excrete large amounts (>10× $10^5$ CFUs) of vegetative cells reaching a maximum between 8 and 10 hours post spore challenge. Although some *C. difficile* spores were excreted in diseased animals, the amounts were negligible (<10% of vegetative CFUs) compared to the high amount of excreted vegetative cells.

FIG. 17 is a graphic representation of data showing that *C. difficile* spores accumulate in the cecum, colon, and feces of CamSA-treated animals. (A) Amount of *C. difficile* spores recovered at different time points following spore challenge from the cecum (white bars) and colon (black bars) of mice treated with 50 mg/kg CamSA. Student's unpaired t-test was used to determine the significance of difference of means. * indicates recovered spores significantly below 72 hour levels (P=0.019; Student's t-test). ** indicates recovered spores significantly below 72 hour levels (P=0.049; Student's t-test). (B) Feces were collected from cages housing five mice challenged with *C. difficile* spores and treated with 50 mg/kg CamSA. Closed bars represent *C. difficile* spores. The amount of *C. difficile* vegetative cells in CamSA-treated animals was negligible (<10% compared to spore counts). Standard deviations represent at least five independent measures. Recovered CFU and recovered spores represent mean values from a pool of five animals.

Recovery of *C. difficile* cells and spores from intestines and feces of CamSA-treated mice. Similar to the hamster CDI model, ingested *C. difficile* spores narrowly localized to the cecum and colon of CamSA treated mice at every time point tested. A negligible amount of *C. difficile* was discovered in the small intestine and stomach. *C. difficile* spores remained in the cecum and colon for 72 hours after spore challenge (FIG. 17A). By 96 hours, the amount of spores recovered from the cecum and colon of CamSA treated animals decreased almost tenfold, from greater than $12 \times 10^5$ to less than $2 \times 10^5$ CFUs.

Consistent with the results from intestinal content, the feces of CamSA-treated animals contained almost exclusively spores (FIG. 17B). In these animals, excretion of ingested *C. difficile* spores started 2 hours post-challenge and continued until at least 96 hours post-challenge. In fact, by 120 hours post-challenge, the sum of excreted *C. difficile* spores was quantitatively identical to the number of spores given by gavage.

FIG. 19 is a graphic representation of the stability of CamSA and taurocholate towards bile salt hydrolases. CamSA (white bar) and taurocholate (black bars) were incubated with cultures of *B. longum* or *L. gasseri*. Percent conjugated bile salts were derived by dividing the intensity of TLC spots obtained at different times by the intensity of the TLC spot obtained at the beginning of incubation (time 0). Time 0 was set at 100% and is not shown for clarity. Standard deviations represent at least five independent measures.

FIG. 20 is a graphic representation of the cytotoxicity of CamSA: Vero cells (white bars) or Caco-2 cells (black bars) were incubated overnight with 10% DMSO, 10% EtOH, 50 µM CamSA or 200 µM CamSA. Cell viability was determined with the CellTiter Glo viability kit. The luminescence signal from DMSO-treated cells was undistinguishable from untreated cells and was set as 100% cell viability. Percent survival for other conditions was calculated relative to untreated cells. Error bars represent standard deviations from at least five independent measurements.

FIG. 21 is a graphic representation of inhibition of *C. difficile* toxin production by CamSA treatment. *C. difficile* spores were incubated overnight in media containing 0 μM CamSA (white bars) or 200 μM CamSA (black bars). The resulting spent media were added to Vero cell cultures and incubated for 24 hours. Cell viability was determined with the CellTiter Glo viability kit. The luminescence signal from untreated cells was set as 100% cell viability. Percent survival for other conditions was calculated relative to untreated cells. Error bars represent standard deviations from at least five independent measurements.

FIG. 22 is a graphic representation that CDI is established between 6 and 9 hours post-infection. (A) Survival of infected mice at 48 hours after challenge with *C. difficile* spores. Mice were treated with 300 mg/kg CamSA at 0, 6, 9, or 12 hours post-challenge. (B) Comparison of CDI severity after 24 hours (white bars) and 48 hours (black bars) for animals challenged with *C. difficile* spores and treated with 300 mg/kg CamSA at 0, 6, 9, or 12 hours post-challenge. Clinical endpoint was set as >6 in the CDI sign severity scale (dashed line). (C) *C. difficile* vegetative cell count in feces of untreated, diseased animals. Feces were collected from cages housing five untreated mice challenged with *C. difficile* spores. Open bars represent *C. difficile* vegetative cells. The amount of *C. difficile* spores excreted by untreated animals was negligible (<10% of vegetative cell counts). Standard deviations represent at least five independent measures. Recovered CFU and recovered spores represent mean values from pools of five animals.

What is claimed:

1. A method of reducing risk of developing *Clostridium difficile*-associated disease or reducing existing *Clostridium difficile*-associated disease in a mammalian subject, the method comprising administering to the mammalian subject an effective amount of a germination-inhibiting compound derived from taurocholate, wherein the compound derived from taurocholate is a compound conforming to:

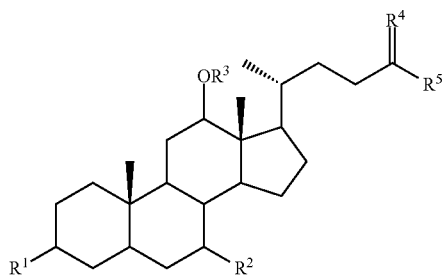

wherein $R^1$ and $R^2$ are hydroxyl groups; $R^3$ is hydrogen; $R^4$ is oxygen; and $R^5$ is $NH(m\text{-}(C_6H_4))SO_3H$.

2. The method of claim 1, further comprising a pharmaceutically acceptable salt.

3. The method of claim 1, wherein the compound is a component of a pharmaceutical composition comprising a pharmaceutically acceptable salt.

* * * * *